(12) United States Patent
Lew et al.

(10) Patent No.: US 10,144,694 B2
(45) Date of Patent: Dec. 4, 2018

(54) METHODS FOR PREPARING PHENOLIC BRANCHED CHAIN ALKYL FATTY ACIDS OR ESTERS THEREOF AND METHODS FOR KILLING MICROORGANISMS

(71) Applicants: The United States of America, as Represented by the Secretary of Agriculture, Washington, DC (US); School of Chemistry and Chemical Engineering—South China University, Guangzhou (CN)

(72) Inventors: Helen N. Lew, Wynnewood, PA (US); Karen Wagner, Ambler, PA (US); Xuetong Fan, North Wales, PA (US); Alberto Nunez, Dresher, PA (US); Robert A. Moreau, Quakertown, PA (US); Michael J. Haas, Wyndmoor, PA (US); Zongcheng Yan, Guangzhou (CN)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/002,249

(22) Filed: Jun. 7, 2018

(65) Prior Publication Data

US 2018/0282254 A1  Oct. 4, 2018

Related U.S. Application Data

(62) Division of application No. 15/057,632, filed on Mar. 1, 2016.

(51) Int. Cl.
*A01N 37/38* (2006.01)
*C07C 51/353* (2006.01)

(52) U.S. Cl.
CPC ............ *C07C 51/353* (2013.01); *A01N 37/38* (2013.01)

(58) Field of Classification Search
CPC .................................................. A01N 37/38
(Continued)

(56) References Cited

U.S. PATENT DOCUMENTS 2,082,459 A  6/1937 Niederl

OTHER PUBLICATIONS

Kohashi, Hitoshi et al., "Addition of Aromatic Compounds to Oleic Acid Catalyzed by Heterogeneous Acid Catalyst," JAOCS, (1984), 61(6): 1048-1051.
(Continued)

*Primary Examiner* — Deborah D Carr
(74) *Attorney, Agent, or Firm* — John Faito; G. Byron Stover

(57) ABSTRACT

Disclosed are methods for preparing phenolic branched chain fatty acids or alkyl esters thereof, involving subjecting in a pressurized container (a) at least one phenolic compound, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof. Also disclosed are methods for killing microorganisms on or in an object, involving contacting said object with an effective microorganisms killing amount of a composition comprising phenolic branched chain fatty acids or alkyl esters thereof, and optionally a carrier; the phenolic branched chain fatty acids or alkyl esters thereof may be produced by the methods described herein.

7 Claims, 10 Drawing Sheets

(58) Field of Classification Search
USPC .................................................... 504/116.1
See application file for complete search history.

(56) References Cited

OTHER PUBLICATIONS

Nakano, Y. et al., "Methanesulfonic Acid Catalyzed Addition of Aromatic Compounds to Oleic Acid," Agricultural Research Services, U.S. Department of Agriculture, Eastern Regiional Research Center, Philadelphia, PA., 19118, 5 pages.

Ngo, Helen L. et al., "Catalytic synthesis and characterization of phenol-branched-chain fatty acide somers," Eur. J. Lipid Sci. Technol., (2014), 116:344-351.

Occolowitz, J.L. et al., "Mass Spectrometry of Naturally Occurring Alkenyl Phenols and Their Derivatives," Analytical Chemistry, (1964) 36(11):2177-2181.

Ionescu, Mihail et al., "Phenolation of vegetable oils," Journal of the Serbian Chemical Society,(2011), 76(4): 591-606.

Stirton, A.J. et al., "Arylstearic Acids From Oleic Acid. Variables Affecting the Yield and Properties," The Journal of the American Oil Chemists' Society, (1948), pp. 365-368.

Zhang, S., et al., I*somerization and Arylation of Oleic Acid on Anion Modified Zirconia Catalysts, Catal Lett, (2009), 127:33-38.

Figure 2
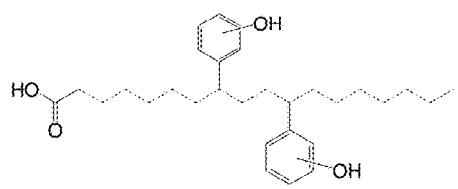
Diaryl-branched-chain FAs [1]
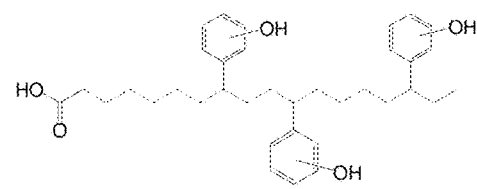
Triaryl-branched-chain FAs [2]

Figure 3

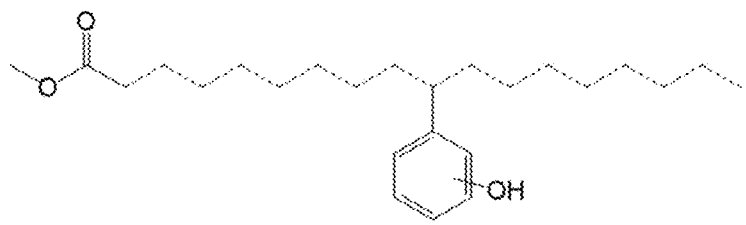

Crude phenolic branched-chain fatty acid
methyl esters [1] (PBC-FAMEs)
Dashed lines indicate several possible positions for the
branching phenolic group

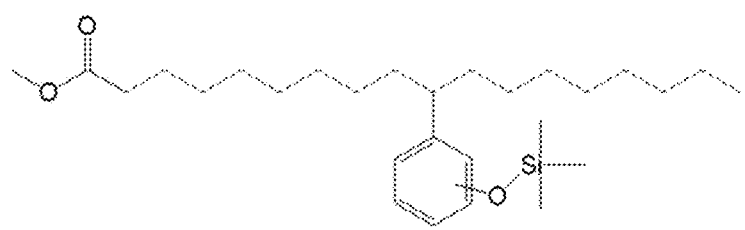

Crude trimethylsilyl phenolic branched-chain
fatty acid methyl esters [2] (TMS-PBC-FAMEs)
Dashed lines indicate several possible positions for
the branching phenolic group

Crude methyl-branched-chain fatty acids [3]
(MBC-FAs)
Dashed lines indicate several possible positions for
the branching methyl group

METHODS FOR PREPARING PHENOLIC BRANCHED CHAIN ALKYL FATTY ACIDS OR ESTERS THEREOF AND METHODS FOR KILLING MICROORGANISMS

This is a divisional of application Ser. No. 15/057,632, filed 1 Mar. 2016, which is herein incorporated by reference in its entirety.

BACKGROUND OF THE INVENTION

Disclosed are methods for preparing phenolic branched chain fatty acids or alkyl esters thereof, involving subjecting in a pressurized container (a) at least one phenolic compound, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain. Also disclosed are methods for killing microorganisms on or in an object, involving contacting said object with an effective microorganisms killing amount of a composition comprising phenolic branched chain fatty acids or alkyl esters thereof, and optionally a carrier; the phenolic branched chain fatty acids or alkyl esters thereof may be produced by the methods described herein.

Vegetable oils and animal fats are excellent feedstocks for the production of biobased products which are environmentally benign; however, the carbon-carbon double bonds in the fatty acids of these lipids are not stable at elevated temperatures and this can limit their applications. Therefore, for many uses they must undergo subsequent reactions in order to have such desirable properties as superior lubricity and good thermal and oxidative stability while maintaining high flash and fire points, high viscosity index numbers, and good biodegradability. In addition, although numerous biobased fluids are commercially available, each displaying unique properties that are suited in applications such as cosmetics, biobased paints, biodegradable lubricants and polymers, metal working fluids, biodiesel, and more (Tullo, A. H., Chemical and Engineering News, 88 (15): 16-19 (2010); Shen, L., et al., Biofuels, Bioprod. Bioref., 25-40 (2010); Frisby, K., The Navy's Environmental Magazine, Winter 2006, pages 48-50; Mittelbach, M., and C. Remschmidt, Biodiesel the comprehensive handbook, Boersedruck Ges.m.b.H, Vienna, Austria (2004)), there is significant interest in developing new chemical classes from these fats and oils. Thus, there is a continuing need to increase the diversity and versatility of biobased industrial fluids by the chemical modification of these fats and oils.

One useful group of fatty acid (FA) derivatives is the branched chain fatty acids (BCFA) in which one or more linear and/or aromatic carbons are attached to the linear carbon chain of the FA. Among the advantages of BCFA relative to their unmodified FA counterparts in industrial applications are their lower melting and cloud points. Recent advances in the processing of agricultural feedstocks have included the development of new paths for the production of BCFA. Most of these processes use homogeneous (e.g., soluble) catalysts or stoichiometric amounts of reagents for functionalization of fatty acids. Rangarajan et al. reported the synthesis of hydroxyl fatty acids, commercially important products in themselves, via epoxidation of unsaturated linear-chain fatty acids (ULC-FAs) followed by ring-opening of the epoxidized products (Rangarajan, B., et al., J. Am. Oil Chem. Soc., 72: 1161-1169 (1995)). The hydroxyl groups were subsequently esterified by alkyl, acyl, or aryl groups to generate hydroxyl ester branched-chain fatty acids. Carboxylic acid esters of these FA may have interesting properties, such as low-temperature fluidity and lubricity. The simultaneous homogeneous acid catalyzed addition of alcohols to epoxidized soybean oil and transesterification of the fatty acyl ester bond to yield hydroxyl ester products with substantially improved low temperature performance has been reported (Hwang, H. S., and S. Z. Erhan, J. Am. Oil Chem. Soc., 78: 1179-1184 (2001); Hwang, H. S., J. Am. Oil Chem. Soc., 80: 811-815 (2003)). Biermann et al. reported the Lewis acid catalyzed additions of alkyl groups (i.e., isopropyl, cyclohexyl, t-butyl and others) to ULC-FAs to give hydro-alkylation products (Biermann, U., and J. O. Metzger, Eur. J. Lipid Sci. Technol., 110: 805-811 (2008)). Ionescu et al. reported alkylation of vegetable oils with phenol in the presence of triflic acid and tetrafluoroboric acid catalysts. This method gave a mixture of phenol alkylated polymerized oil (30-60%), phenyl esters (<10%), and unreacted oil (30%) (Ionescu, M., and Z. S. Petrovic, J. Serb. Chem. Soc., 76: 591-606 (2011)).

Heterogeneous (i.e., solid phase) catalytic approaches have also been used for upgrading fats and oils. Roe et al. reported the first example of heterogeneously catalyzed branching of ULC-FA by condensing a phenolic compound with oleic acid (OLA) with an ion-exchange resin, leading to an approximately 30% yield of phenyl-branched-fatty acids (Roe, E. T., et al., J. Am. Oil Chem. Soc., 36: 656-659 (1959)) which were reported to have antioxidant properties. Kohashi et al. reported the addition of aromatic compounds to fatty acid double bonds by heterogeneous acid clay catalysts to give aryl-branched-chain fatty acids (ABC-FAs) (Kohashi, H., J. Am. Oil Chem. Soc., 61: 1048-1051 (1984)). In 1995, Alink reported the catalytic arylation of OLA with aromatic hydrocarbons (i.e., xylenes) in the presence of clay catalysts (i.e., Montmorillonite K10, Clarion 470 and 550) to give xylylstearic acid products with up to 90% yields (Alink, B. A. O., U.S. Pat. No. 5,440,059 (1995); U.S. Pat. No. 5,840,942 (1998)). Unfortunately, the clay catalysts used by Alink cannot be recycled and reused. In 1991, Alink disclosed an arylation of OLA with aromatics (i.e., toluene, xylenes, and phenol) using highly acidic perfluorinated resins grafted with sulfonic acid (Alink, B. A. O., U.S. Pat. No. 5,034,161 (1991)); however, although these resin catalysts gave relatively high yields (80%) of the ABC-FA products, the amount of catalysts needed were equal to that of the OLA used in the reaction. Zhang et al. reported the arylation and isomerization of OLA with aromatic species (i.e., toluene) in the presence of zeolite (i.e., Cu-Beta and H-Beta) and anion modified zirconia catalysts to give a mixture of SBC-FAs (saturated branched chained-FAs (alkyl substituted)) and ABC-FAs (Zhang, Z., WO 2005/014766 A2 (2005), U.S. Patent Application Publication 2007/0015928); however, the simultaneous production of both products (i.e., SBC-FAs (alkyl substituted) and ABC-FAs)) led to only moderate yield of ABC-FA products. More recently, Zhang reported the use of another catalytic system, anion modified sulfated and tungstated zirconia catalysts, to obtain a maximum conversion of OLA of 78.4 wt % after 6 h at 250° C. (Zhang, S., Catal. Lett., 127: 33-38 (2009)); however, this system still concurrently produced both products (i.e., SBC-FAs (alkyl substituted) and ABC-FAs)) which led to only moderate yield of ABC-FA products of 38.2 wt %.

Thus, it is still important to develop new synthetic approaches to improve the production of aryl-branched-chain fatty acids while minimizing the production of other byproducts such as dimer and lactones. We have developed new synthetic approaches and have found that the resulting aryl-branched-chain fatty acids, particularly the phenolic branched-chain fatty acids (PBC-FAs), can be used against foodborne diseases.

Foodborne diseases are a public health concern affecting a large number of people and resulting in significant economic cost in the United States and worldwide. It is estimated by the Centers for Disease Control and Prevention (CDC) that foodborne illnesses in the United States cause about 48 million sicknesses, 128,000 hospitalizations, and 3,000 deaths each year (Scallan, E., et al., Emerging Infectious Diseases, 17(1): 7-15 (2011)). Three recent studies provided cost-of-foodborne-illness estimates ranging from $14.1 billion to $152 billion (Hoffmann, S., et al., J. Food Protect., 75(7): 1291-1302 (2012); Hoffmann, S., and T. D. Anekwe, Making sense of recent cost-of-foodborne-illness estimates, EIB-118, U.S. Department of Agriculture, Economic Research Service, September 2013; Scharff, R., Health-related costs from foodborne illness in the United States, Produce Safety Project, Georgetown University, Washington, D C, 2010; Scharff, R., J. Food Protect., 75(1): 123-31 (2012)). Bacteria that have been frequently associated with the outbreaks of foodborne diseases include both Gram-negative and Gram-positive bacteria such as *Escherichia coli* O157:H7, *Listeria monocytogenes, Salmonella* spp., *Staphylococcus aureus, Clostridium perfringens*, and *Campylobacter* spp. (CDC, Centers for Disease Control and Prevention, Food Safety, 2011).

One of the major challenges for ensuring microbial food safety is the limited effectiveness of common sanitizers used by the industry which are capable of only achieving 1-2 log reduction of common pathogens in many foods (Beuchat, L. R., et al., J. Food Protect., 67: 1238-1242 (2004)). There are many possible reasons for this limited ability to inactivate pathogens in food. One of the reasons is that bacterial cells are able to protect themselves, with the bacterial cell membrane acting as a diffusion barrier between the cytoplasm and the extracellular medium. The integrity of this membrane is crucial for the survival of bacteria as the disruption of the cell membrane would result in cell injury and death. The cell membrane consists of a phospholipid bilayer with embedded proteins. Membranes are usually impermeable for most hydrophilic compounds (ions), a property which is essential for controlling the composition of the cytoplasm, although small hydrophilic compounds can be transported into cells through various protein channels such as porins (Konings, W. N., et al., Antonie van Leeuwenhoek, 81: 61-72 (2002); Galdiero, S., et al., Curr. Protein Pept. Sci., 13: 843-854 (2012)). In addition, there is a concern about the use of chlorine (a common sanitizer) by the food industry and other industries due to the potential environmental and health risks associated with the formation of potentially harmful chlorine by-products (Olmez, H., and U. Kretzschmar, LWT-Food Sci. Technol., 42, 686-693 (2009)). Chlorine reacts with organic matter and forms potential carcinogenic products such as trichloromethane (Richardson, S. D., et al., Water Air Soil Pollut., 123: 95-102 (2000); Hua, G., and D. A. Reckhow, Water Res., 41: 1667-78 (2007)). For this reason, chlorine is banned for use on certain food products in many EU nations. Furthermore, there is an increasing demand for novel environmentally friendly antimicrobials from renewable resources produced by clean and sustainable technology. With increasing environmental awareness and emphasis on sustainability and renewability, natural or bio-based active compounds are becoming more attractive.

Phenolics and medium-chain fatty acids are naturally occurring compounds commonly found in plants and are by-products of food processing. A few of these compounds, such as cinnamaldehyde, thymol and carvacrol, have antimicrobial properties (Burt, S., Intl. J. Food Microbiol., 94(3): 223-53 (2004); Di Pasqua, R., et al., J. Agric. Food Chem., 55: 4863-4870 (2007); Yun, J., et al., J. Food Sci., 78: M458-M364 (2013)). However, these antimicrobial compounds are volatile and possess unpleasant characteristic odors which prevent their use in the food industry. Medium chain fatty acids are also known to have antimicrobial proprieties; however, their antimicrobial ability is relatively low (Kabara J. J., and D. L. Marshall, Medium chain fatty acids and esters, IN: P. M. Davidson, J. N. Sofos, A. L. Branen, (Eds.), Antimicrobials in Foods, 3rd ed., Taylor and Francis, Roca Raton, Fla. (2005), pp. 327-360).

We found that our synthetically prepared phenolic branched-fatty acids (PBC-FAs) mixtures surprisingly had antimicrobial properties against microorganisms (e.g., Gram-positive and Gram-negative bacteria).

SUMMARY OF THE INVENTION

Disclosed are methods for preparing phenolic branched chain fatty acids or alkyl esters thereof, involving subjecting in a pressurized container (a) at least one phenolic compound, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain. Also disclosed are methods for killing microorganisms on or in an object, involving contacting said object with an effective microorganisms killing amount of a composition comprising phenolic branched chain fatty acids or alkyl esters thereof, and optionally a carrier; the phenolic branched chain fatty acids or alkyl esters thereof may be produced by the methods described herein.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

FIG. 2 shows the poly-PBC-FAME (phenolic branched chain fatty acid methyl ester) products as described below.

FIG. 3 shows chemical structures of major components in the crude PBC-FAMEs, crude TMS-PBC-FAMEs and crude SBC-FAs as described below.

FIG. 9A control (5% ethanol), FIG. 9B 0.9 ppm crude PBC-FAs, FIG. 9C 3.6 ppm crude PBC-FAs, and FIG. 9D 232 ppm crude SBC-FAs.

DETAILED DESCRIPTION OF THE INVENTION

Figure 1:
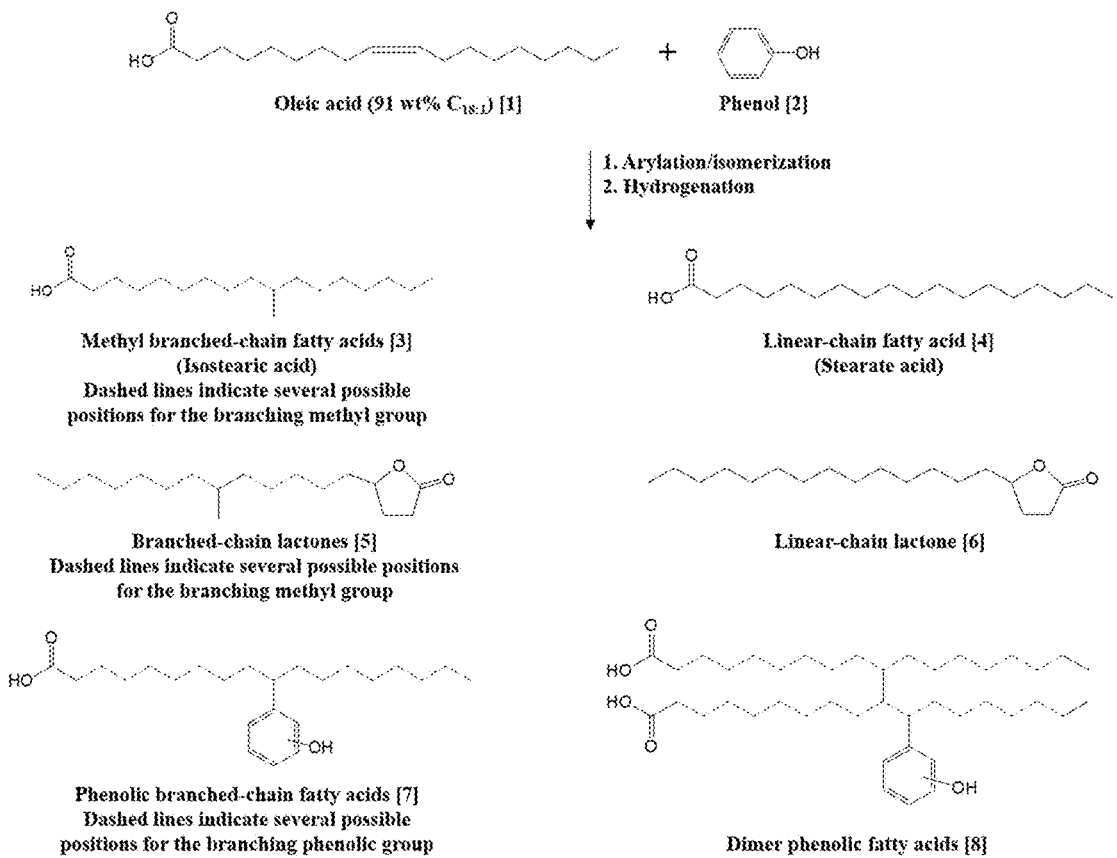
FIG. 1 shows products of the isomerization and arylation of OLA with phenol as described below.

Disclosed are methods for producing phenolic-branched chain fatty acids or alkyl esters thereof, the methods involving subjecting in a pressurized container (a) at least one phenolic compound, (b) unsaturated fatty acids having 10 to 25 carbon atoms, alkyl esters thereof, or mixtures thereof, and (c) H-ferrierite zeolite catalyst in the presence of distilled water or alcohol, and a nitrogen atmosphere at a temperature of about 100° C. to about 400° C. (e.g., 100° to 400° C.; preferably about 150° to about 300° C. (e.g., 150° to 300° C.); more preferably about 200° to about 260° C. (e.g., 200° to 260° C.)) and a pressure of about 10 to about 1000 psi (e.g., 10 to 1000 psi; preferably about 25 to about 500 psi (e.g., 25 to 500 psi); more preferably about 50 to about 300 psi (e.g., 50 to 300 psi)), and isolating saturated phenolic branched chain fatty acids or alkyl esters thereof or mixtures thereof; wherein the ratio of said at least one phenolic compound: said unsaturated fatty acids or alkyl esters thereof is about 100 to about 1 (e.g., 100 to 1; preferably about 50 to about 1 (e.g., 50 to 1); more preferably about 20 to about 1 (e.g., 20 to about 1)), wherein the yield of said saturated phenolic-branched chain fatty acids is greater than about 70 wt % (e.g., greater than 70 wt %).

Also disclosed are methods for killing microorganisms on or in an object, involving contacting said object with an effective microorganisms killing amount of a composition comprising phenolic branched chain fatty acids or alkyl esters thereof, and optionally a carrier. The phenolic branched chain fatty acids or alkyl esters thereof may be produced by the methods described herein.

The unsaturated fatty acid used as the starting material is generally a fatty acid having unsaturated bonds and a total carbon number of 10 to 25, preferably a total carbon number of 16 to 22. Considering industrial applications, it is preferable that the major component of the starting material has an average carbon number of 18. Unsaturated fatty acids having a total carbon number of this range are useful as starting materials for the synthesis of PBC-FAs for use in, for example, coating materials, corrosion inhibitors, lubricants, and as dietary and healthy fat, etc. With respect to the degree of unsaturation (i.e., the number of unsaturated carbon-carbon bonds), any unsaturated fatty acid may be used as long as one or more such bonds are present in the molecule. Preferably, the number of unsaturated bonds is generally 1 to 3, preferably 1; oleic acid and erucic (22:1) are the most preferable. Without being bound by theory, the presence of an unsaturated bond in the molecule causes the formation of a carbocation as an intermediate, thereby facilitating the skeletal isomerization reaction; if a phenolic compound is used in large quantities as a starting material, formation of this intermediate carbocation is hampered, thereby making it difficult for isomerization and dimerization to proceed.

Unsaturated fatty acids which may be used include, for example, oleic acid, palmitoleic acid, erucic acid, elaidic acid, linoleic acid, linolenic acid, and undecenoic acid, which can be derived from beef tallow, palm oil, safflower oil, sunflower oil, tall oil, rapeseed oil, soybean oil, fish oil, or the like. A mixture that may be used as the starting material is, for example, a mixture containing two or more of these unsaturated fatty acids, or a mixture containing one or more of these unsaturated fatty acids and one or more saturated fatty acids such as palmitic and stearic acids, various esters of the aforementioned unsaturated fatty acids, and the like. In the case of a mixture, the content of the above-mentioned unsaturated fatty acids is generally not less than about 40% by weight (e.g., not less than 40% by weight), preferably not less than about 50% by weight (e.g., not less than 50% by weight), preferably not less than about 60% by weight (e.g., not less than 60% by weight), preferably not less than about 70% by weight (e.g., not less than 70% by weight), and most preferably not less than about 80% by weight (e.g., not less than 80% by weight) in view of reaction rate and yield. These amounts are not meant to be limiting, and increments between the recited percentages are specifically envisioned as part of the invention.

Alkyl esters of unsaturated fatty acids having a total carbon number of 10 to 25 which may be used as a starting material are those corresponding to the above-described unsaturated fatty acids. In other words, alkyl esters of the unsaturated fatty acids exemplified above can be used. Although the alkyl moiety is not subject to limitation as to carbon number, its carbon number is generally 1 to 4, preferably 1. Specific examples of alkyl esters include, for example, methyl esters, ethyl esters, propyl esters, and butyl esters of the above-mentioned unsaturated fatty acids, with preference given to methyl esters.

When a mixture is used as the starting material, generally a mixture that contains at least one alkyl ester of the above-described fatty acids is used. Specifically, it is a mixture of one or more alkyl esters of these unsaturated fatty acids, or a mixture containing at least one alkyl ester of these unsaturated fatty acids and saturated fatty acids, various esters, etc. In the case of a mixture, the content of alkyl esters of the above-mentioned unsaturated fatty acids is normally not less than about 40% by weight (e.g., not less than 40% by weight), preferably not less than about 50% by weight (e.g., not less than 50% by weight), preferably not less than about 60% by weight (e.g., not less than 60% by weight), preferably not less than about % by weight (e.g., not less than 70% by weight), and most preferably not less than about 80% by weight (e.g., not less than 80% by weight) in view of reaction rate and yield. These amounts are not meant to be limiting, and increments between the recited percentages are specifically envisioned as part of the invention.

From the viewpoint of reaction selectivity, it is preferable that the above-described starting material be alkyl esters of octadecenoic acid, such as methyl oleate and methyl elaidate, or a mixture thereof.

Phenolics which may be used include, for example, phenol, thymol, carvacrol, creosol, guaiacol, hydroxybenzoic acid, gallic acid, vanillic acid or the like. They have one or more hydroxyl groups on the aromatic ring. They can also have other substituents (R, R') on the hydroxyl aromatic ring including alkyl groups which can be a saturated or unsaturated or conjugated straight chain, a saturated, unsaturated or conjugated branched chain, cyclic and/or aromatic. These phenolic compounds may also include additional functional groups to the hydroxyl aromatic ring such as amino ($-NH_2$), secondary amino ($-NRH$; R=alkyl groups which can be a saturated or unsaturated or conjugated straight chain, a saturated or unsaturated or conjugated branched chain, cyclic and/or aromatic), tertiary amino ($-NRR'$; R and R'=alkyl groups which can be a saturated, unsaturated or conjugated straight chain, a saturated or unsaturated or conjugated branched chain, cyclic and/or aromatic), carboxylic acid ($-RCO_2H$; R=alkyl groups which can be a saturated, unsaturated or conjugated straight chain, a saturated or unsaturated or conjugated branched chain, cyclic and/or aromatic, esters ($-RCOOR'$; R,R'=alkyl groups which can be a saturated, unsaturated or conjugated straight chain, a saturated or unsaturated or conjugated branched chain, cyclic and/or aromatic), ethers ($-OR$; R=alkyl groups which can be a saturated, unsaturated or conjugated straight chain, a saturated or unsaturated or conjugated branched chain, cyclic and/or aromatic), halogens (fluoro ($F^-$), chloro ($Cl^-$), bromo ($Br^-$), iodo ($I^-$)), hydroxyl ($-OH$), oxygen, nitrogen, sulfonyl ($-SO_2-$) and thiols ($-S-$) substituents. The phenolics which may be used also include but are not limited to cresol, 2,6-ditert-butylphenol, 2,6-ditert-butyl-4-methylphenol, 2,6-ditert-butyl-4-ethylphenol, anisole, and the like; (2) two or more adjacent R groups may be joined, forming a multi-ring structure, these rings may or may not be aromatic, as in the cases of 2-hydroxynaphthalene and tocopherols, respectively, and can be homo- or heterocyclic. In addition, other compounds may be used include those with 2 or 3 hydroxyl group on the ring (such as catechol, gallic acid, caffeic acid) and those with additional aldehyde and acid groups (such as coumaric acid and syringic acid). Economically, the preferred phenolics will be relatively cheaper phenolics such as simple phenol, hydroxybenzaldehyde, carvacrol, thymol, vanillin, or vanillic acid.

In the present invention, generally, ferrierite type zeolites are preferred from the viewpoint of heat resistance, acid resistance, and acid properties. The term "ferrierite type zeolite" as used herein is a zeolite composed of two-dimensional alumina-silica network structure, with interconnecting channels between the 8-membered-ring (MR) and 10-MR structures (Bekkem, H. V., Introduction to Zeolite Science and Practice, 2nd Edition, Elsevier, New York, N.Y., 2001, pp. 1033-1053). The channels of commercially available ferrierites typically contain an alkali metal (Na or K) or ammonium ($NH_4$) cation. For example, we examined K-containing ferrierite with a silica/alumina ($SiO_2/Al_2O_3$) molar ratio of 17.5 and $NH_4$-containing ferrierite with a silica/alumina ($SiO_2/Al_2O_3$) molar ratio of 20. Although these zeolites can be synthesized by hydrothermal synthesis (J.C.S., 2158 (1948)), they are also commercially available.

Although it is preferable from the viewpoint of catalyst activity that the cation in a zeolite be a proton, a zeolite of the potassium and ammonium types, or the like, may be used in the reaction after being converted into the proton type by ion exchange. Zeolites may be used in the reaction after a pretreatment by ion-exchange and calcination.

The $SiO_2/Al_2O_3$ molar ratio of zeolite is preferably about 3 to about 300 (e.g., 3 to 300), more preferably about 5 to about 100 (e.g., 5 to 100). The ratio is preferably not less than about 3 (e.g., not less than 3) in view of catalytic activity, and not more than about 300 (e.g., not more than 300) in view of yield. The "silica/alumina ratio (molar)" can easily be determined by atomic absorption photometry. The preferred zeolite is H-ferrierite zeolite.

Generally, employing the above-described zeolite, the reaction is carried out in the presence of water or a lower alcohol (e.g., alcohols having 1 to 4 carbon atoms, for example methanol, ethanol, propanol, butanol, etc. are preferred, with a greater preference given to those alcohols having the same alkyl group as that of the starting fatty acid esters to be isomerized). Without being bound by theory, this presence of water or alcohol is to suppress acid anhydride formation due to dehydration or dealcoholation of the starting material; this suppression is attributable to acid point modification of the zeolite, such as conversion of Lewis acid point into Brönsted acid point. It is preferable to use water or an alcohol when the starting material is unsaturated fatty acids or esters of unsaturated fatty acids.

The process is generally carried out at about 100° to about 400° C. (e.g., 100° to 400° C.; preferably about 150° to about 300° C. (e.g., 150° to 300° C.); more preferably about 200° to about 260° C. (e.g., 200° to 260° C.)) with a catalyst loading of at least about 1 wt % up to about 50 wt % (e.g., 1-50 wt %); preferably about 5 wt % up to about 30 wt % (e.g., 5-30 wt %); more preferably about 10 wt % up to about 20 wt % (e.g., 10-20 wt %)), and about 1% to about 1000% water (e.g., 1 to 1000%) or a lower alcohol, preferably about 1 to about 800% (e.g., 1 to 800%), and more preferably about 1% to about 650% (e.g., 1 to 650%), based on about 100 parts by weight (e.g., 100 parts by weight) of the above-described unsaturated fatty acids and/or alkyl esters thereof. These amounts are not meant to be limiting, and increments between the recited numbers and percentages are specifically envisioned as part of the invention.

Also, the reaction may be carried out in a closed system where the reaction pressure is generally about 10 to about 1000 psi (e.g., 10 to 1000 psi); preferably about 25 to about 500 psi (e.g., 25 to 500 psi); more preferably about 50 to about 300 psi (e.g., 50 to 300 psi)) and with a cooling sleeve (i.e., condenser) at the reactor head where the temperature is about −50° C. to about 25° C. (e.g., −50 to 25° C.); preferably about −30° C. to about 0° C. (e.g., −30 to 0° C.); more preferably about −15° C. to about −18° C. (e.g., −15 to −18° C.)) in order to prevent vaporization of water, alcohols and other low boiling substances in the system including those substances contained in a catalyst. These amounts are not meant to be limiting, and increments between the recited numbers are specifically envisioned as part of the invention.

Since the catalyst tends to be poisoned by coke, the reaction normally takes about 1 to about 100 hours (e.g., 1 to 100 hours; preferably about 3 to about 72 hours (e.g., 3 to 72 hours); more preferably about 6 to about 48 hours (e.g., 6 to 48 hours)). These amounts of reaction time are not meant to be limiting, and increments between the recited numbers are specifically envisioned as part of the invention. The catalyst may be recycled using methods known in the art.

The reaction apparatus used is preferably pressurized (e.g., an autoclave) because a pressurized reaction system is preferred. The atmosphere in the autoclave is preferably replaced with nitrogen or argon.

The product obtained by the above-described arylation reaction contains phenolic-branched chain saturated fatty acids and/or esters thereof, when the starting material is unsaturated fatty acids and/or esters thereof, in a high yield. The product further contains linear-chain fatty acids, lactones and dimer acids (polymeric phenolic fatty acids or esters) when the starting material is unsaturated fatty acids and/or esters thereof. The phenolic-branched chain fatty acids, etc., thus obtained normally have phenol side chains of 1 to 6 carbon atoms. They are obtained as a mixture of many isomers with different branching positions.

Furthermore, phenolic-branched chain saturated fatty acids (esters of branched chain saturated fatty acids, when the starting material is unsaturated fatty acids and/or esters thereof) can be isolated as follows. Generally, the catalyst zeolite is removed by filtration. The crude product is purified by removing excess phenolic materials by distillation or steam stripping, followed by any known method, such as the compression method, the Emerson method, or the Henkel method (U.S. Pat. No. 2,293,674; U.S. Pat. No. 2,421,157; U.S. Pat. No. 2,800,493; J. Am. Oil Chem. Soc., 45, 471 (1968)) or recrystallization method to remove the linear chain fatty acid components, to yield phenolic-branched chain saturated fatty acids (esters of phenolic-branched chain saturated fatty acids, when the starting material is unsaturated fatty acids and/or esters thereof) of high purity.

The yield of the saturated phenolic-branched chain fatty acids is generally >about 60 wt % (e.g., >60 wt %); >about 61 wt % (e.g., >61 wt %); >about 62 wt % (e.g., >62 wt %); >about 63 wt % (e.g., >63 wt %); >about 64 wt % (e.g., >64 wt %); >about 65 wt % (e.g., >65 wt %); >about 66 wt % (e.g., >66 wt %); >about 67 wt % (e.g., >67 wt %); >about 68 wt % (e.g., >68 wt %); >about 69 wt % (e.g., >69 wt %); >about 70 wt % (e.g., >70 wt %); preferably >about 71 wt % (e.g., >71 wt %); preferably >about 72 wt % (e.g., >72 wt %); preferably >about 73 wt % (e.g., >73 wt %); preferably >about 74 wt % (e.g., >74 wt %); preferably >about 75 wt % (e.g., >75 wt %); preferably >about 76 wt % (e.g., >76 wt %); preferably >about 77 wt % (e.g., >77 wt %); preferably >about 78 wt % (e.g., >78 wt %); preferably >about 79 wt % (e.g., >79 wt %); preferably >about 80 wt % (e.g., >80 wt %) preferably >about 81 wt % (e.g., >81 wt %). These amounts are not meant to be limiting, and increments between the recited percentages are specifically envisioned as part of the invention.

The yield of dimers (e.g., 7 in FIG. 1) is generally <about 15 wt % (e.g., <15 wt %); preferably <about 14 wt % (e.g., <14 wt %), <about 13 wt % (e.g., <13 wt %), <about 12 wt % (e.g., <12 wt %), <about 11 wt % (e.g., <11 wt %), <about 10 wt % (e.g., <10 wt %), <about 9 wt % (e.g., <9 wt %), <about 8 wt % (e.g., <8 wt %), <about 7 wt % (e.g., <7 wt %), <about 6 wt % (e.g., <6 wt %), <about 5 wt % (e.g., <5 wt %); <about 4 wt % (e.g., <4 wt %); <about 3 wt % (e.g., <3 wt %). These amounts are not meant to be limiting, and increments between the recited percentages are specifically envisioned as part of the invention.

The yield of lactone is generally <about 15 wt % (e.g., <15 wt %); preferably <about 14 wt % (e.g., <14 wt %), <about 13 wt % (e.g., <13 wt %), <about 12 wt % (e.g., <12 wt %), <about 11 wt % (e.g., <11 wt %), <about 10 wt % (e.g., <10 wt %), <about 9 wt % (e.g., <9 wt %), <about 8 wt % (e.g., <8 wt %), <about 7 wt % (e.g., <7 wt %), <about 6 wt % (e.g., <6 wt %), <about 5 wt % (e.g., <5 wt %); <about 4 wt % (e.g., <4 wt %); <about 3 wt % (e.g., <3 wt %). These amounts are not meant to be limiting, and increments between the recited percentages are specifically envisioned as part of the invention.

The yield of linear chain fatty acid is generally <about 18 wt % (e.g., <18 wt %); preferably <about 17 wt % (e.g., <17 wt %); <about 16 wt % (e.g., <16 wt %); <about 15 wt % (e.g., <15 wt %); <about 14 wt % (e.g., <14 wt %), <about 13 wt % (e.g., <13 wt %), <about 12 wt % (e.g., <12 wt %), <about 11 wt % (e.g., <11 wt %), <about 10 wt % (e.g., <10 wt %), <about 9 wt % (e.g., <9 wt %), <about 8 wt % (e.g., <8 wt %), <about 7 wt % (e.g., <7 wt %), <about 6 wt % (e.g., <6 wt %), <about 5 wt % (e.g., <5 wt %); <about 4 wt % (e.g., <4 wt %); <about 3 wt % (e.g., <3 wt %). These amounts are not meant to be limiting, and increments between the recited percentages are specifically envisioned as part of the invention.

The conversion of the unsaturated fatty acids or alkyl esters thereof is generally >about 85% (e.g., >85%); >about 86% (e.g., >86%); >about 87% (e.g., >87%); >about 88% (e.g., >88%); >about 89% (e.g., >89%); >about 90% (e.g., >90%); >about 91% (e.g., >91%); >about 92% (e.g., >92%); >about 93% (e.g., >93%); >about 94% (e.g., >94%); >about 95% (e.g., >95%); >about 96% (e.g., >96%); >about 97% (e.g., >97%); >about 98% (e.g., >98%); >about 99% (e.g., >99%). These amounts are not meant to be limiting, and increments between the recited percentages are specifically envisioned as part of the invention.

Also disclosed are methods for killing microorganisms on or in an object, the method involving contacting (e.g., application to the surface or into an object) said object with an effective microorganisms killing amount of a composition comprising phenolic branched chain fatty acids or alkyl esters thereof, and optionally a carrier.

Objects treated by the methods described herein include surfaces. Objects treated by the methods described herein also include foods and beverages. Foods and beverages treated by the methods described herein include meat, poultry, seafood, eggs, nuts, fruits and vegetables. Particularly included are apples, melons, apricots, peaches, pears, artichokes, beans, bell peppers, carrots, celery, tomato, lettuce, and spinach. Foods particularly include fresh-cut produce (e.g., fruits and vegetables) which is produce that has been, for example, peeled, cut, sliced, or shredded. The fresh-cut produce may be subsequently made into juice, or dried or dehydrated or frozen by methods known in the art. Objects treated by the methods described herein also include drinks, food-packages, non-food products (cosmetics, pharmaceuticals, sanitizers, etc.). Objects treated by the methods described herein also include a surface, such as a kitchen countertop.

Preferably the foods have been processed (i.e., are not in their natural state such as whole melons). Typically, fruits and vegetables are subjected to various processing techniques wherein they are subjected to disorganization of their natural structure, as by peeling, cutting, comminuting, pitting, pulping, freezing and dehydrating.

Contacting or exposing objects such as foods (e.g., fresh-cut produce) with the antimicrobial composition described herein (to reduce and/or kill bacteria) may occur by conventional methods such as spraying or dipping or immersion wherein the object such as food (e.g., fresh-cut produce) is in contact with the antimicrobial solution for a certain period of time (e.g., about 120 seconds).

A wide range of application rates of the compositions may be suitable in accordance with the present methods. Those working in this field would of course be readily able to determine in an empirical manner the optimum rates of application for any given combination of target microorganisms to be killed or eliminated. The amount of composition used will be at least an effective amount to reduce and/or kill microorganisms. The term Aeffective microorganisms killing amount@ as used herein, means the minimum amount of composition needed to reduce and/or kill the number of microorganisms on in an object or area (e.g., soil, structures, plants, or agricultural commodities such as grain or wood). Of course, the precise amount of the composition needed will vary in accordance with the particular composition used; the type of object to be treated; the number of days of effectiveness needed; and the environment in which the object is located. The precise amount of the composition can easily be determined by one skilled in the art given the teaching of this application. Other compounds may be added to the composition provided they do not substantially interfere with the intended activity of the composition; whether or not a compound interferes with activity can be determined, for example, by the procedures described below.

The optional carrier may be, for example, agronomically or physiologically or pharmaceutically acceptable carriers known in the art.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and methods: All of the reagents were obtained from commercial sources and used without further purification. OLA (91.2 wt % C18:1, 6.1 wt % C18:2, 2.7 wt % saturated fatty acids), methanol, and phenol were purchased from Aldrich Chemical Co. (Milwaukee Wis.). Tridecanoate methyl ester (C13:0) was obtained from NU Chek Prep, Inc. (Elysian, Minn.). Sulfuric acid was obtained from Mallinckrodt Baker Co. (Phillipsburg, N.J.). Crisco® brand soybean oil was purchased from a local market. Linoleic acid (99 wt % C18:2) was a gift from Nippon Oils and Fats Co. Ltd. Linolenic acid (9.63 wt % C16:0, 6.77 wt % C18:0, 30.3 wt % C18:1, 16.5 wt % C18:2, 1.41 wt % C20:0, 35.4 wt % C18:3) was obtained from MP Biomedicals, LLC. (Solon, Ohio). Ferrierite zeolite (HSZ-720KOA, potassium ($K^+$), 17.5 mol/mol $SiO_2/Al_2O_3$ was obtained from Tosoh Co., Tokyo, Japan) and CP914C, ammonium ($NH_4^+$), 20 mol/mol $SiO_2/Al_2O_3$ was obtained from Zeolyst International, Conshohocken, Pa.). Ethyl acetate, N,O-bis(trimethylsilyl)trifluoroacetamide (BSTFA), phenol, dimethylsulfoxide (DMSO), and thiazolyl blue tetrazolium bromide were purchased from Sigma-Aldrich (St. Louis, Mo.). McFarland 0.5 standards were purchased from Thermo Fisher Scientific (Pittsburgh, Pa.). Tryptic soy agar (TSA) and Tryptic soy broth (TSB) were purchased from Becton, Dickinson and Company (Franklin Lakes, N.J.). Bacterial cultures listed in Table 5 were obtained from American Type Culture Collection (ATCC) (Manassas, Va.) with the exception of *Pseudomonas tolaasii* which was supplied by Pennsylvania State University (University Park, Pa.) and *Priopionibacterium acnes* NRRL B-4224, supplied by the Northern Regional Research Laboratory of the USDA, Peoria, Ill.).

General procedure for the preparation of crude PBC-FAs (i.e., oleic-phenol BCFAs): Detailed procedures to convert a potassium-containing zeolite to a protonated cation form (H-ferrierite zeolite) by acid washing were reported previously (Ngo, H. L., et al., Eur. J. Lipid Sci. Technol., 108: 214-224 (2007); Ngo, H. L., et al., Eur. J. Lipid Sci. Technol., 2012, 114, 213-221 (2012)). In general, crude PBC-FAs were prepared by adding a mixture of unsaturated fatty acids or alkyl esters thereof (e.g., OLA; 30 g), phenolic compound(s) (e.g., phenol). 60 g, 6 molar equivalents to, for example, OLA), modified $H^+$-Ferrierite-K zeolite (4.5 g, 15 wt % to, for example, OLA), and deionized water (3.25 mL, 73% to $H^+$-Ferrierite-K) to a 300 mL high pressure stainless steel reactor equipped with a temperature controller and mechanical stirrer. The reactor head had a cooling sleeve (i.e., condenser) attached which allowed the temperature to be set between $-5°$ C. and $-20°$ C. The vessel was sealed, purged with $N_2$ (80 psi, 3×), the headspace was filled with $N_2$ (80 psi), and the mixture was heated with stirring to the desired temperature. Small fractions of the reaction mixture were removed from the reactor at 6 and 24 h for hydrogenation, methylation, and analysis. After 48 h, the heating was discontinued, the mixture was allowed to cool to room temperature, and the system was vented. After removal of the zeolite catalyst by vacuum filtration, samples of the crude mixture (oleic-phenolic BCFAs (FIG. 1)) were subjected to hydrogenation and methylation. It is important to note that the phenolic-branched-chain fatty acid products (FIG. 1, structures 7 and 8) in the crude mixture obtained upon removal of the zeolite catalyst were actually in the saturated form. The subsequent reactions (i.e., hydrogenation and methylation) were performed only for the purpose of analysis. Thus only small amounts of the crude phenolic product were carried on to these next two steps: Hydrogenation was performed with small amounts (approximately 1 wt %) of 5% palladium on carbon (Pd/C) catalyst (Pressure Chemical Co., Pittsburgh, Pa.) and hydrogen gas (20 psi, room temperature, 3 h) to give the crude saturated form of the FA mixture. The saturated fatty acid product was then converted to fatty acid methyl esters (FAME) by methylation, which involved treating the product with excess methanol (100 fold molar excess) and a catalytic amount of sulphuric acid at 100° C. for 2 h. After heating, the excess methanol was evaporated and the crude product was diluted with 20 mL hexanes:ethyl acetate (95:5) and neutralized with 20 mL saturated sodium bicarbonate solution. The mixture was transferred to a separatory funnel for extraction. The aqueous phase was back-extracted with hexanes:ethyl acetate (95:5) after which the two solvent phases were combined and washed with the distilled water one more time. The organic phase was dried with magnesium sulfate and solvent was evaporated to give quantitative yield of the desired crude PBC-FAME product. The structures of the crude PBC-FAME mixture can be found in FIG. 1 but in the fatty acid form. The methylated products were then subjected to analysis by various analytical techniques described below.

Procedure to purify the crude PBC-FA products for bacterial studies: The excess phenol was removed from the crude PBC-FA mixture using a wiped film molecular distillation. The circulator of the main evaporator jacket of the distillation was set to 80° C.; the residue and feed jackets were set to 80° C.; and the condenser was set to 50° C. The vacuum system of the distillation device was allowed to reach below $5.0\times10^{-3}$ mbar, and the wiper motor was set to 300 rpm before the feed was started. The mixture (508.3 g) was fed at a rate of one drop per two seconds through the distillation at a maximum vacuum pressure with the diffusion pump below $8.3\times10^{-3}$ mbar. The crude PBC-FAs (435.4 g) were recovered from distillation. The proposed structures for this crude mixture are shown in FIG. 1.

General procedure for the preparation of crude poly-PBC-FA products (i.e., soybean-phenol BCFAs): The reaction conditions used to prepare and purify soybean-phenol BC-FAs are similar to the reaction conditions described in the oleic-phenol BCFA procedure but with minor modifications. In general, a mixture of unsaturated fatty acids or alkyl esters thereof derived from soybean oil, phenolic compound(s) (e.g., phenol, 6 molar equivalents to, for example, soybean fatty acids), modified $H^+$-ferrierite zeolite (10 wt % to, for example, soybean fatty acids), and deionized water (% to $H^+$-ferrierite) to a 300 mL high pressure stainless steel reactor equipped with a temperature controller and mechanical stirrer. The reactor head had a cooling sleeve (i.e., condenser) attached which allowed the temperature to be set at −5° C. The vessel was sealed, purged with $N_2$ (80 psi, 3×), filled with $N_2$ (80 psi), and heated with stirring to the desired temperature. After 24 h, the zeolite was removed from the oil mixture to yield the crude soybean-phenol BCFAs, predominantly containing poly-PBC-FAs (FIG. 2). The term "poly" is used because there are more than one phenol on the fatty alkyl chain (FIG. 2). The excess phenol could be distilled by vacuum distillation using either the wiped film molecular distillation device (conditions described from above) or the traditional vacuum distillation device set at temperature between 70 to 90° C. at 1-2 torr. Both distillation methods could efficiently remove the excess phenol down to <5.0 wt %. This procedure could also be applied to other phenolic BCFA products presented in Table 4.

Procedure for the synthesis of the trimethylsilyl-phenolic branched-chain fatty acid methyl esters (TMS-PBC-FAMEs): A mixture of 300 mg crude PBC-FAMEs, 245 μL (1.2 equiv.) BSTFA and 500 μL pyridine were mixed in a 4 dram vial, sealed and heated at 75° C. for 2 h. The mixture was purified using the extraction method described in the crude PBC-FAME procedure. This reaction resulted in quantitative yield of the crude TMS-PBC-FAMEs (FIG. 3, structure 2).

Procedure for the synthesis of the crude methyl-branched-chain fatty acid mixture (crude SBC-FAs): Detailed experimental procedure for the synthesis of crude SBC-FA mixture can be found in the previously reported paper (Ngo et al., 2012; Ngo and Foglia, 2014). In brief, a mixture of 50 g OLA (FIG. 1, structure 1), 2.5 g (5.0 wt % to OLA) modified H-Ferrierite zeolite, 188 mg (7.5 wt % to zeolite) triphenylphosphine, and 1.8 mL (72% to $H^+$-Ferrierite) distilled water was added to a 600 mL high pressure stainless steel Parr reactor (Parr Instrument, Moline, Ill.) equipped with a controller and mechanical stirrer. The reactor was sealed, purged with nitrogen (80 psi, 3×), jacketed with 80 psi nitrogen, and heated to 260° C. for 4 h. The reaction mixture was allowed to cool down to room temperature. The zeolite catalyst was removed by vacuum filtration. The oil product was dried with magnesium sulfate. The solvent was then removed by an evaporator to give the crude SBC-FA product (FIG. 3, structure 3) at quantitative yield.

Chromatographic characterization of crude PBC-FAs: Gas chromatography with flame ionization detector (FID) (Model 6890 Hewlett Packard, now Agilent Technologies, Santa Clara Calif.) was used to determine the wt % composition of products in the crude mixture. GC-MS with electron impact ionization (Model GC-7890A and MS-5975C VL-MSD with triple-axis detector, Agilent Technologies) was used to determine the molecular weight of the mono-branched fatty esters using methods that were previously reported by Ngo et al. (Ngo, H. L., et al., Eur. J. Lipid Sci. Technol., 108: 214-224 (2007); Ngo, H. L., et al., Eur. J. Lipid Sci. Technol., 2012, 114, 213-221 (2012)).

Reverse phase HPLC was conducted using an Agilent 1100 HPLC, with autosampler, with an Agilent Model 1100 diode-array UV-visible detector operated at 280 nm (Agilent Technologies, Avondale, Pa.) and an Agilent Series 1200 ELSD (Evaporative Light Scattering Detector) operated at 40° C., with nitrogen gas at a pressure of 3.5 bar. The column was a Prevail C18 3μ column (2.1×150 mm, Alltech Associates, Deerfield, Ill.) operated at a flow rate of 0.2 ml/min. The gradient mobile phase components were methanol (A) and water (B), with a gradient timetable as follows: 0 min, 90/10 A/B, v/v; 40 min, 100/0; 50 min, 100/0, 51 min, 90/10; 60 min 90/10. Eluting materials were analyzed online by MS (Model 1100 MSD, Agilent Technologies), operating with an atmospheric pressure chemical ionization (APCI) chamber in the positive ion mode with the following parameters: 200-1000 m/z, fragmentor 5V, drying gas: nitrogen at 6 liters/min, nebulizer pressure 60 psi, drying gas temperature 350° C., vaporizer temperature 325, capillary voltage 4000 V and corona current 4 amps. HPLC-MS with electrospray ionization (ESI) was also used, in which case solvent A (methanol) was premixed with 20 mM ammonium formate, and all other gradient conditions were the same as above. ESI was conducted with the following ionization parameters: 200-1200 m/z, fragmentor 5 V, drying gas: nitrogen at 10 liters/min, nebulizer pressure 20, drying gas temperature 300° C., and capillary voltage 4000 V.

Propagation of bacteria: Frozen bacteria cultures obtained from ATCC and Pennsylvania State University were regrown in TSB for 22 h at 28° C. for *Pseudomonas* and at 37° C. for the rest of the bacteria with agitation and then streaked onto TSA plates. The TSA plates were incubated at 37° C. for 18-22 h (28° C. for *Pseudomonas*) to form single colonies. These colonies were then used to inoculate fresh TSB and grown for 18-22 h at 37° C. (28° C. for *Pseudomonas*). The cell density of the starting inocula was determined by serial dilution with sterile phosphate buffered saline (PBS) and spread plating on TSA. Colonies on the TSA plates were recorded after 18-22 h at 37° C. except for *Pseudomonas* which was incubated at 28° C.

Determination of minimum inhibitory concentrations (MICs) and minimum bactericidal concentrations (MBCs): MICs and MBCs were determined by micro-dilution method using serially diluted tested compounds according to the Clinical and Laboratory Standards (CLSI, Clinical and Laboratory Standard Institute, Methods for dilution antimicrobial susceptibility tests for bacteria that grow aerobically, 6th Edition, CLSI Document M7-A6, 2003, Wayne, Pa.) and Magalhaes and Nitschke (Magalhaes, L., M. and Nitschke, Food Control, 29: 138-142 (2013)). Inocula were grown from refrigerated stocks using growth conditions described earlier. Cells were pelleted by centrifugation at 2,182×g for 10 minutes resuspended in 9.9 mL PBS, and serially diluted in PBS. Culture dilutions were adjusted to approximately 2×10⁶ CFU/mL using McFarland 0.5 standard and plated on TSA to confirm viable cell concentration. Test compounds (Table 8) were dissolved in ethanol or DMSO and diluted with PBS to give a concentration of 1000 μg/mL. This solution was further diluted in PBS to give concentrations of 1, 2, 4, 8, 16, 32, 64, 128, 256, and 512 μg/mL. An equimolar mixture of unreacted phenol and OLA was also tested as a comparison. Positive control (wells containing the growth medium, PBS with 5% ethanol and inocula) and negative control (wells containing the growth medium, 5% ethanol and PBS without inocula) were maintained for each test batch. Microdilution plate wells containing 100 μl TSB and 100 μl diluted test compounds were inoculated with 20 μl of 2×10⁶ CFU/mL bacterial suspension. Microplates were covered and incubated for 24 h at 37° C. (28° C. for *Pseudomonas*) with 100 rpm orbital shaking. At least 3 independent replicates of quadruplicate tests were conducted. 20 μl of 0.1% thiazolyl blue tetrazolium bromide in water was added to each well and plates were allowed to sit at ambient temperature for 1 h. The MICs were the lowest test compound concentration for which no color change (no active growth) occurred. To determine MBCs, the contents in the wells showing no growth were spread plated on TSA and incubated at 37° C. for 24 h (28° C. for *Pseudomonas*). The lowest concentration that yielded no bacterial colonies was recorded as MBC.

Growth curves of *L. innocua* as affected by crude phenolic branched-chain fatty acid mixture: Crude PBC-FAs and crude SBC-FAs were diluted as described as in MIC/MBC determination. A microplate reader (BioTek Synergy HT, Winooski, Vt.) was used for incubation and reading of microplates. Incubation was performed at a temperature of 37° C. for a period of 24 h with shaking. The plate reader was attached to a computer system for automatic measurement and analysis. Absorbance was measured at 600 nm at intervals of 1 h.

Antimicrobial test: Twenty microliters of *E. coli* ATCC 25922 and *Listeria innocua* ATCC 33090 with populations of 9.4 and 9.3 log CFU/ml, respectively, were added to 1 ml of 0.1% and 0.01% phenol fatty acid, 0.1% phenol and 0.1% OLA prepared as described above. Since the solutions contained 10% of ethanol, ethanol (10%) along with water were used as references. The bacteria and the solutions were vortexed and incubated at ambient temperature (~22° C.) for 5 min before immediately being plated (diluted when needed) on TSA to determine the survival of the bacteria. After 24 h at 37° C., colonies on the plates were counted.

Statistical analysis: Data on antimicrobial test were subjected to statistical analysis using SAS Version 8.2 (SAS Institute, Cary, N.C.). The Duncan's multiple range test was used for the treatment effects.

Results and discussion: PBC-FA isomers were synthesized in one step by treating OLA with excess equivalents of phenolic compounds. FIG. 1 showed arylation of OLA to phenolic compound to give a mixture of products. The compositions of the products were established by GC. While the GC/MS was used to characterize the mono-branched chain FA isomers (FIG. 1, structures 3, 4, 5, 6 and 7), and LC-MS data supported the formation of the dimer products (FIG. 1, structure 8). Detailed characterization of the products is described below. As shown in Table 1, entry 1, the reaction was performed with the following conditions: 1.2:1 molar ratio of phenol to OLA, H⁺-Ferrierite-K zeolite, and distilled water, after 24 h of reaction the products of both isomerization and addition reactions were observed affording a mixture of SBC-FA (29.5%) and PBC-FAs (26.5%), and a moderate OLA conversion of 87.6%. The high level of lactone (25.9%) was observed due to moderate conversion (Entry 1). When the reaction was carried out at a 2:1 phenol to OLA molar ratio, a conversion of 86.4% of OLA was surprisingly obtained, the yield of SBC-FAs surprisingly decreased to 18.8%, and the PBC-FA isomers was obtained in a slightly higher yield of 35.2% (Entry 2). These surprising results indicated that the use of increased amounts of phenol should drastically improve the yield for the production of PBC-FAs. Thus a reaction was conducted at a molar ratio of phenol to OLA of 4:1 and the results surprisingly showed 99% conversion and an increase in the yield of PBC-FAs to 63.3% (Entry 3).

We then increased the phenol equivalent to 6 and performed the reaction for 6 to 48 h. For the 6 h reaction, surprisingly PBC-FA isomers were afforded in 33.3% yield and 87.6% conversion (Entry 4). Prolonging the reaction time to 24 h surprisingly led to a significant increase of PBC-FA yield to 67% yield and 98.7% OLA conversion (Entry 5). Increasing the reaction time further surprisingly led to enhanced PBC-FAs yield (72.3% for the 48 hour reaction) (Entry 6).

We also attempted to reduce the catalyst loading to 5 wt %. Unfortunately, a significant drop in PBC-FAs selectivity to 35.2% was surprisingly obtained and the conversion of OLA was also reduced (85.7%) (Entry 7). It should be noted that other byproducts including branched-chain and linear-chain lactones (FIG. 1, structures 5 and 6), and dimer phenolic products (FIG. 1, structure 8) were also surprisingly obtained. The yield of lactone byproducts was surprisingly decreased by increasing the phenol equivalents, reaction time, and catalyst loading.

We also attempted to improve the catalytic activity and yield of the reactions by increasing catalyst loadings (Table 1). At least 6 equivalents of phenol to OLA were used in Table 1 because that surprisingly gave the highest yield for the production of PBC-FAs. At a 15 wt % H⁺-Ferrierite-K catalyst loading, the conversion and yield surprisingly increased to 93.6% and 42.5%, respectively, after heating at 200° C. for 6 h (Entry 7). Prolonging reaction times to 24 h surprisingly gave 99% conversion of OLA and a yield for PBC-FAs of 73.9% (Entry 8). However, further increasing the reaction time surprisingly did not lead to enhanced PBC-FA yields (Entry 9). Increasing the phenol to OLA molar ratio to 8:1 in reactions containing 15 wt % catalyst also surprisingly did not seem to increase the PBC-FA yield (entries 10-12). In an effort to further improve the reaction activity, we carried out experiments with even higher catalyst loadings, i.e., 20 wt % (Entries 13-21). Unfortunately, we surprisingly only observed slightly higher yield (Entries 13-15). When the reaction temperature was increased from 200° C. to 250° C., the degree of conversion surprisingly increased significantly to >99% after only 6 h; unfortunately, surprisingly the yield for phenolic-branched-chain products fell to only a modest 59.6-64.5% (Entries 16-18) and this was accompanied by an increase in dimer phenolic byproducts. Entries 19-21 showed that the arylation reaction surprisingly also worked well with unsaturated fatty acid methyl esters (i.e., methyl oleate). In the presence of H⁺-Ferrierite-K catalyst, methyl oleate was reacted with phenol to surprisingly give a majority of PBC-FA isomeric products after 48 h and in comparatively high conversions (>99%).

This process has also been surprisingly demonstrated to work with reaction scales ranging from 10 g to 800 g. As shown in Table 2, the modified H⁺-Ferrierite-K catalyzed addition reaction was performed with 6:1 molar ratio of phenol to OLA, 15 wt % H⁺-Ferrierite-K zeolite, and small amounts of distilled water at 200° C. Under these reaction conditions, 70.9 wt % (average of 4 replicates) of the phenolic branched-chain fatty acids (FIG. 1, structures 7&8) and 29.2 wt % (average of 4 replicates) of the byproducts (FIG. 1, 3-6) were surprisingly obtained. Table 2, entries 1-4 list the four replicates to show its reproducibility. The excess phenols were removed by distillation and could be reused in subsequent reactions.

Table 3 shows the optimized reaction conditions for the arylation of unsaturated fatty acids that were obtained from hydrolysis of soybean oil (Christie, W. W., Lipid analysis: isolation, separation, identification, and structural analysis of lipids, 1982, Pergamon, New York). The composition of the mixture of soybean FAs was 14.8 wt % C16:0, 7.03 wt % C18:0, 22.8 wt % C18:1, 43.2 wt % C18:2, 5.96 wt % C18:3, and 6.21 wt % unknown. It is important to note that only 78.2 wt % of the fatty acids in the oil were available for arylation reaction as the oil contained 21.8 wt % of saturated fatty acids that cannot undergo arylation reactions. Therefore, the equations to calculate the conversions and yields of the products were different from the OLA results. Table 3, entries 1-3 showed the reactions performed with $H^+$-Ferrierite-K zeolite (5 wt % to OLA), phenol (6 equivalents to OLA), and distilled water at 200° C. After 6 h of reaction, the percent yields of products 5.1 wt % lactones, 37 wt % PBC-FAs, and 6.0 wt % dimer-phenolic-FAs, to lead to a moderate conversion of 48% (Entry 1) Surprisingly, when the reaction was allowed to heat for an additional 12 h, the yield of PBC-FAs and conversion of soybean FAs went up to 56 wt % and 85%, respectively (Entry 2). However, the conversion (92%) and yield (62 wt %) surprisingly only slightly improved after 48 h of reaction at 200° C. (Entry3). Interestingly, this mixture was similar to the OLA system and detailed characterization of these products is discussed below. We then increased the catalyst loading to 10 wt % and the conversion and yield surprisingly gave 100% and 68 wt %, respectively (Entries 4-6). At 15 wt % catalyst loading, a complete conversion (100%) of fatty acid was surprisingly also obtained after 48 h of reaction; however, the yields of PBC-FAs surprisingly did not increase at higher catalyst loadings and they appeared to level off at ~71 wt % (Entries 7-9). Control experiments were carried out at a 15 wt % H-Ferrierite without the addition of water and a complete conversion (100%) was also surprisingly obtained (Entry 12). These results surprisingly indicated that water was not needed for achieving high conversions, but it is still needed in order to achieve high yield of the phenolic branched-chain fatty acids (Entries 10-12).

Although the $H^+$-Ferrierite-K zeolite catalyst system reported in Table 3 was sufficient in catalyzing the arylation reaction, the acid solution pretreatment zeolite method was very labor intensive and generated a lot of aqueous water waste. Therefore, the Ferrierite zeolite containing ammonium cations was examined, and it can be easily pretreated at 500° C. for 5 h to obtain the active protonated form. This new catalyst system was called $H^+$-Ferrierite-$NH_4$-500. This pretreatment heat process was much easier to work with than the acid treatment process. Also for this study, mixed fatty acids derived from soybean oil were used as a feedstock instead of OLA to help improve the economics of the process. Table 4 shows the results synthesized from the $H^+$-Ferrierite-$NH_4$-500 zeolite catalyst. The results showed that this zeolite catalyst was surprisingly just as effective as $H^+$-Ferrierite-K catalyst. With 10 wt % catalyst loading, the reaction surprisingly gave 100% conversion of soybean fatty acids and 73 wt % poly-PBC-FAs (Entry 1). Interestingly, when we scaled up the reaction 10 times, the yield dropped slightly but this could also be within the experimental error (Entry 2). Entry 3 is a replicate of entry 2 but with a slightly higher amount of distilled water. Unfortunately, the results remained similar to entry 2. This system also worked with safflower fatty acids and various phenolics (Table 4, Entries 4-7).

Although these poly-PBCFA products could be successfully synthesized at high yields and conversions, it is important to thoroughly characterize this complex mixture by addressing two major questions. First, were there more than one phenols on the alkyl chain in the PBC-FA products? Second, were there any phenol groups on the dimer acid compound? To address these questions, feedstock containing predominantly linoleic and linolenic acids were investigated. The results showed that the product mixture for the linoleic system was very similar to the crude soybean-phenolic BCFA products (Entry 8). But interestingly, the mixture for the linolenic system was very different (Entry 9). Almost an equal ratio between the PBC-FA and dimer-PBC-FA products was surprisingly obtained.

Figure 4:
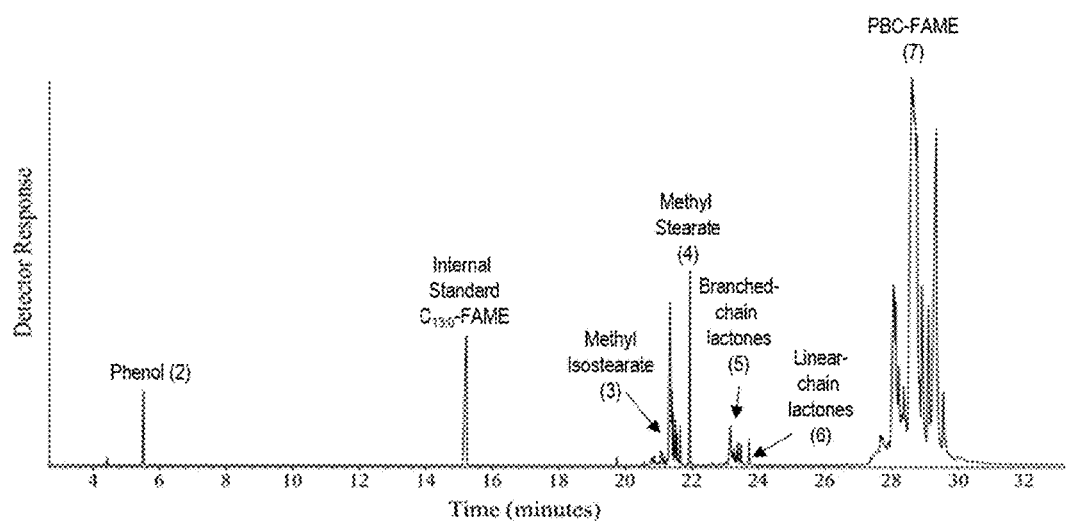
FIG. 4 shows the GC-MS (gas chromatography-mass spectrometry) spectrum of the crude hydrogenated methylated PBC-FAME (fatty acid methyl ester) mixture (from OLA) as described below.

GC and GC-MS analysis: FIG. 4 is the GC chromatogram resulting from the injection of the methylated reaction products. The early elution of a single peak at approximately 15.7 minutes (tridecanoate methyl ester internal standard) was followed by a series of unresolved peaks between 21 and 24 minutes. This group of peaks had the elution profile and mass spectra that correspond to isomeric methyl-methylheptadecanoates, eluting approximately between 21.0 and 21.7 minutes, methyl stearate at approximately 21.9 minutes, isomeric hydroxy-methyloctadecanoates between 22.8 and 23.6 minutes, and the γ-stearolactone at approximately 23.7 minutes, as reported previously by Ngo et al. (Ngo, H. L., et al., Eur. J. Lipid Sci. Technol., 108: 214-224 (2007); Ngo, H. L., et al., Eur. J. Lipid Sci. Technol., 2012, 114, 213-221 (2012)).

Upon MS analysis of the GC eluate, the group of peaks eluting between 27 and 31 minutes displayed a consistent molecular ion ($M^{+\bullet}$) at m/z 390, the mass expected for an OLA-phenol adduct, with the characteristic loss of $CH_3O^\bullet$ (M-31) expected for a fatty acid methyl ester (FAME). The reaction of phenol with a fatty acid could result in the formation of the phenyl ester of OLA. The spectrum for this product would have a $M^{+\bullet}$ at m/z 360, the ion corresponding to the α-cleavage of the phenol (M-93), and would also display a peak characteristic of the phenol ion fragment (m/z 94). Peaks corresponding to these ions were not detected in the GC-MS traces (FIG. 4), indicating that esterification of OLA with phenol did not occur under the conditions examined here. Consequently, the presence of the $M^{+\bullet}$ at m/z 390 in the group of peaks between 27 and 31 minutes was considered as strong evidence that the addition of the phenol occurred only at the alkyl chain level. The complexity of the GC-MS pattern in the 27-31 min region (FIG. 4) suggested that the aryl addition was not localized to any single site on the OLA chain but rather occurred in any of multiple possible locations.

Figure 5:
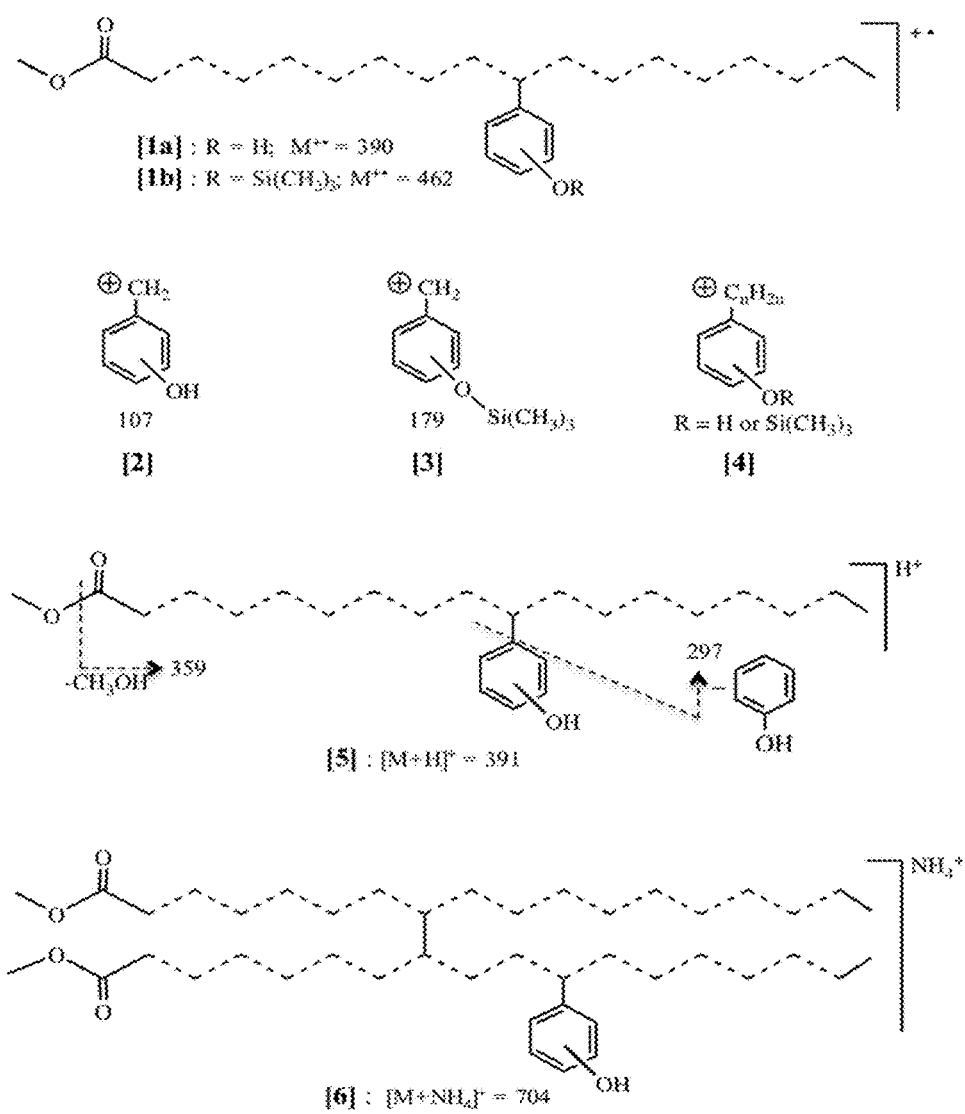
FIG. 5 shows structures of phenolic-fatty acid adducts that are consistent with the mass spectra as described below. Structures 1a&b represent the crude PBC-FAME products before and after silylation, respectively, as described below.

Depending on the mechanism of the reaction, the linkage of phenol to the alkyl chain of the fatty acid could be through either an ether or a carbon-carbon bond. If the reaction generated the carbon-carbon bond, then it would leave the hydroxyl group on the phenol available for subsequent reactions. On the other hand, if the reaction gave the ether product, then the hydroxyl group would not be observed. These two reaction alternatives were distinguished by silylation and analysis of the reaction products. The GC-MS elution profile of the silylated products was similar to that of the underivatized products (chromatogram not shown), but lacked the $M^{+\bullet}$ at m/z 390 and showed instead a $M^{+\bullet}$ at m/z 462. This was consistent with addition of the $Si(CH_3)_3$ silyl group (72 atomic mass units (u)) as would be expected upon addition of $Si(CH_3)_3$ to the hydroxyl group of phenol. This clearly evidenced the formation of a carbon-carbon bond upon addition of phenol to the alkyl chain, as represented in FIG. 5, structures 1a&b for the PBC-FAME products before and after silylation, respectively. In these structures, the dashed line indicates the different site alternatives in the alkyl chain for the addition of the phenol to form positional isomers. Also, it should be noted that the link to the alkyl chain could be at the ortho, meta, or para position of the phenol, as represented in FIG. 5.

Figure 6:
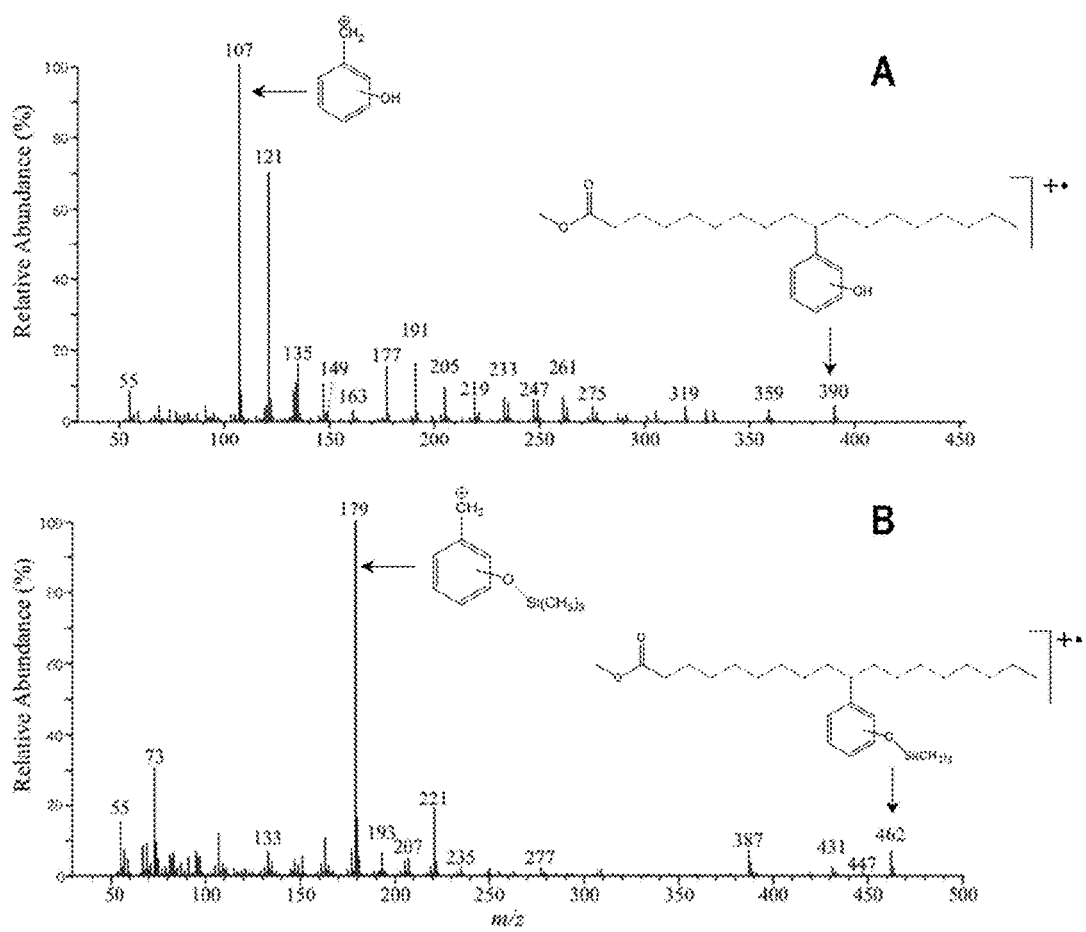
FIG. 6 shows the MS (mass spectrometry) spectra of the underivatized (FIG. 6A) and silylated PBC-FAME (FIG. 6B) products, as described below.

Further evidences for the arylation of the alkyl chain were found in the MS spectra of the underivatized and the silylated PBC-FAME products, FIGS. 6a and 6b, respectively. The electron impact ionization spectra corresponding to the reaction products before silylation had a prominent fragment ion at m/z 107 (FIG. 6a) that was shifted 72 u to produce the ion at m/z 179 for the silylated sample (FIG. 6b). Based on previous studies on alkyl phenol products, we identified structures 2 and 3 in FIG. 5 for the underivitized and silylated fragments ions, respectively (Kingston, E. E., et al., Org. Mass Spectrom., 20: 351-359 (1985); Occolowitz, J. L., Anal. Chem., 36: 2177-2181 (1964)). Both spectra fragment ions at m/z 107 and 179 in FIG. 6 had a characteristic ion series associated with 14 atomic mass units increases, consistent with the —$CH_2$— components of an alkyl chain as represented by structure 4 in FIG. 5. The spectra corresponding to the PBC-FAME products eluting in the chromatogram in FIG. 4, and the silylated derivative, basically differed in the intensities of the peaks in this alkyl ion series. These intensity differences reflected fragmentation patterns associated with the particular isomers formed in the reaction, but according to the GC-MS results it was difficult to clearly identify the position of the phenyl group on the alkyl chain or the reaction site on the phenyl ring. Consequently we can only report the general structure 1 for the PBC-FAME products as shown in FIG. 5.

The products were also analyzed by GC using a high temperature column which allowed for higher molecular weight product scanning. The chromatogram (not shown) revealed that there were late eluting products that can be associated with the addition of more than one phenol and/or the formation of dimers. These late eluting products were not analyzed by MS due to the temperature limitations on the column used with the GC-MS and the extensive fragmentation expected for higher MW molecules under electron ionization mass spectrometry, which made it difficult to observe the corresponding M. Consequently HPLC-MS with a soft ionization method was used instead.

Figure 7:
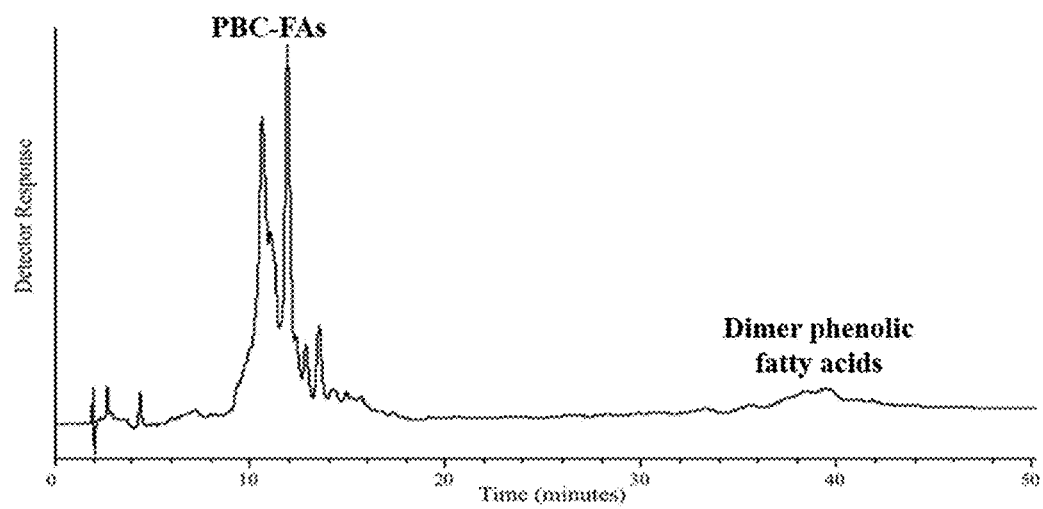
FIG. 7 shows a reversed phase HPLC (high performance liquid chromatography) chromatogram with UV detection (280 nm) of the crude PBC-FAME products (from oleic acid) as described below.

HPLC analysis: Reverse phase HPLC chromatography with UV detection (FIG. 7) showed a group of peaks between 9 and 18 minutes and a second group approximately between 36 and 44 minutes. Both groups of peaks had absorption $\lambda_{max}$ at approximately 280 nm which was consistent with a phenol presence on the products. HPLC-MS with APCI in the positive mode showed that the first group of peaks consisted of protonated molecules $[M+H]^+$ at m/z 391 and breakdown fragments at m/z 359 and 297, corresponding to the loss of $CH_3OH$ and phenol, respectively. This corresponded to the cleavage of the methyl ester bond and the loss of attached phenol from the parent molecule, as indicated for structure 5 in FIG. 5.

The second group of peaks (36-44 min retention time) did not have a clear APCI spectrum and thus ESI was used, with ammonium formate as modifier. The resulting MS spectra from peaks in the 36-44 min region of the HPLC pattern exhibited an $[M+NH_4]^+$ peak at m/z of 704, which is consistent with a dimer structure as 6 (FIG. 5) with only one phenol addition. We also characterized the products using the same analytical methods as for the OLA system. Surprisingly, the GC-MS analyses of the hydrogenated and methylated products indicated that a majority (95 wt %) of the product was mono-branched-chain fatty acid phenol addition products (FIG. 7) and only very small amounts (<5 wt %) of oligomers of branched-chain fatty acid phenol addition products (FIG. 7) were generated in the reaction mixtures. The yields (or selectivity) of branched-chain fatty acid phenol addition products were estimated based on GC integrations as we have not been able to separate the monomeric and oligomeric branched-chain fatty acid phenol addition products. We also analyzed the samples using HPLC-MS and ESI without adding ammonium formate. Instead of a peak at m/z 704, $[M+NH_4]^+$, we saw a major peak at m/z 709, which was consistent with the $[M+Na]^+$ peak of the dimer structure of 6 in FIG. 5. In addition to the m/z 704 and 709 ions with and without ammonium formate, we also observed m/z 702 and 707 ions (with and without ammonium formate, respectively), which may correspond to the dimer similar to the structure of 6 but with either a new carbon-carbon double bond or a cyclic derivative of structure 6, FIG. 5.

Thus we have successfully synthesized PBC-FA isomers at surprisingly high yields and high conversions. The presence of isomeric PBC-FAs in the product mixtures can potentially lower their melting points, which is important for biobased applications that require good fluidity at lower temperatures.

Phenol addition to fatty acid with more than one double bonds was investigated by utilizing a mixture of fatty acids containing oleic, linoleic, and linolenic acid (C18:1, C18:2 and C18:3, 20%, 16% and 50%, respectively) as substrates for the reaction. GC-MS is of limited ability to analyze the formed product because the high temperatures involved in the analysis could produce degradation of the products. Also the electron ionization mode used by the instrument mass spectrometer can produce ions that are not representatives of the products formed because of the fast fragmentation produced by this technique as the molecules increase in size. Consequently, HPLC with ESI (electrospray ionization) was used in a quadrupole-time of flight (Q-TOF) mass spectrometer. Each sample was analyzed as a free acid and as a methyl esters. For the free acid form ESI in the negative ion mode produced $[M–H]^-$ allowing the detection for the formation of products carrying the addition of more than one phenol to the polyunsaturated fatty acids. Accordingly, the products with one addition for C18:1, C18:2, and C18:3 were observed at m/z 375, 373, and 371, two additions (C18:2 and C18:3) at m/z 467 and 465, and the triple addition to the C18:3 at m/z 559. Because the HPLC-MS chromatogram cannot produce a resolved separation of these products, the yield of the reaction can only be estimated by the intensity of the ions under the eluting peak containing the products; therefore, surprisingly the addition of one phenol was the major product with approximately 74% of yield, double additions with approximately 25% of yield, and <1% yield for the triple addition to C18:3.

Figure 8:
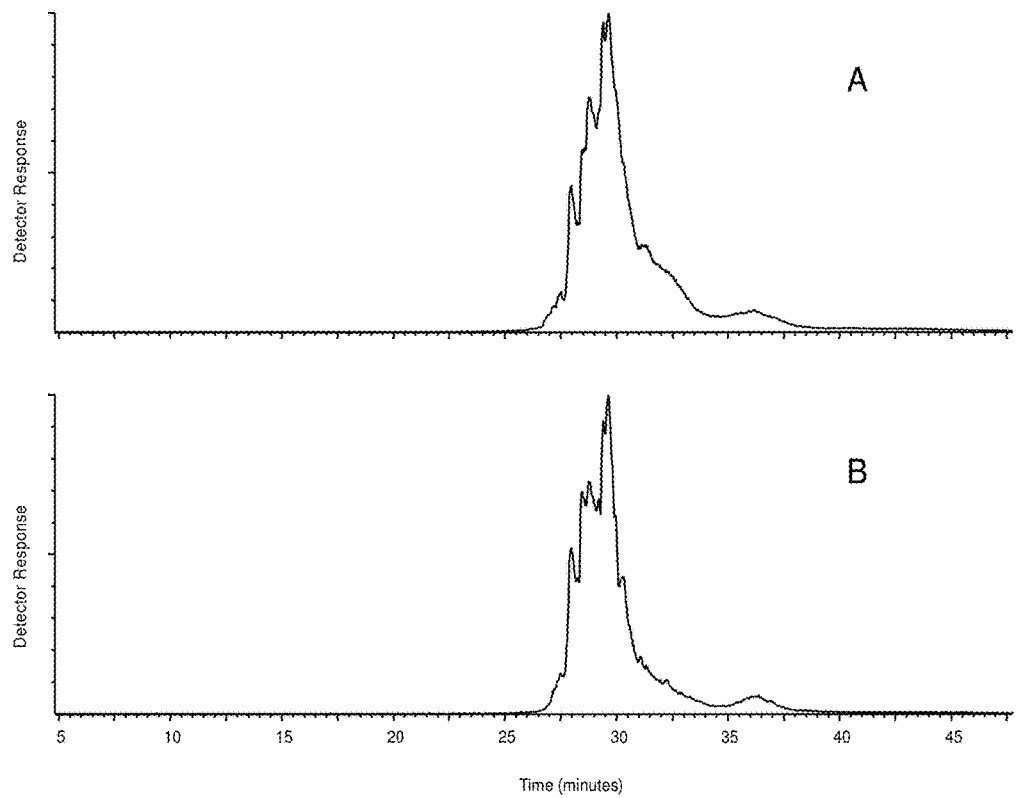
FIG. 8 shows reversed phase HPLC chromatograms with UV detection (280 nm) of the ion extracted chromatogram at m/z 107 of the crude PBC-FAMEs from linoleic acid (FIG. 8A) and the ion extracted chromatogram at m/z 107 of the crude PBC-FAMEs and poly-PBC-FAMEs from soybean fatty acids (FIG. 8B) as described below.

The analysis of products from the free acid by HPLC-MS in negative mode did not produce a good ionization for the detection of dimers, consequently the methyl esters of linoleic acid and soybean were analyzed in positive mode using ammonium formate to produce the $[M+NH_4]^+$ adduct. The spectra of the formed products (monomers and dimers) in this reaction had a fragmented product ion at m/z 107, similar to the one observed in the GC-MS analysis (FIG. 6A). Using collision energy of 15 eV the intensity of this ion was enhanced, allowing the plotting of the extracted ion chromatogram at m/z 107. FIG. 8A and FIG. 8B are the extracted ion chromatograms corresponding to the methyl esters of linoleic and soybean fatty acids showing a broad peak between 25 and 35 min. followed by a smaller and broader peak at 36 min. For both substrates the chromatograms were very similar, although different from the chromatogram in FIG. 6A because the columns and method used were different. Under the first broad peak (25-35 min) for both samples the one and two-phenol additions were observed. Soybean oils contain approximately 6-7% C18:3 but the triple addition of phenol to this fatty acids could not be confirmed because of its low abundance. However, the confirmation of dimers with one phenol addition, as shown in FIG. 5, structure 6 can be obtained from the mass spectra of both samples under the broad peak at 36 min. The dimer surprisingly represented between 4-6% of the total of the phenol derivative products. Not enough evidence could be obtained for the confirmation of a dimer with two-phenol addition but it is expected to be present at low concentrations.

Compounds which may be produced by our methods have many applications. For example, hydroxyphenylstearic acid (HPS) can be furthered processed to be used as coating materials (Scholnick, F., et al., JAOCS, 42: 23-24 (1964)). Furthermore, HPS has been incorporated in ester oils for refrigerators in order to provide corrosion inhibiting effects; HPS acid or salts thereof with alkaline earth metals has been incorporated in hydrocarbons or diesters in order to provide oxidation stability and rust inhibiting effects; salts of HPS acid and aliphatic amines have incorporated in gasoline fuels to provide corrosion inhibiting effects; salts of HPSacid and N,N-disubstituted amines have incorporated in jet fuel to provide corrosion inhibiting effects (Kohashi, H., U.S. Pat. No. 4,888,132 (1989). Hydroxyphenyloleic (HPO) acid has been used as a developer for making a lithographic printing plate (Kondo, T., and H. Miura, U.S. Pat. No. 5,068,164 (1991)). Hydroxyphenyloleic (HPO) acid has also been used as an aqueous rust inhibitor (https://data.epo.org/publication-server/rest/v1.0/publication-dates/19881214/patents/EP0294649NWA1/document.html). Phenyl stearic acid has been used to treat textiles so that stains (including salad oil, motor oil, butter, lipstick, cranberry juice, and grass) were easily washed out (Swidler, R., et al., U.S. Pat. No. 3,870, 555 (1975)).

Chemically synthesized phenolic branched-chain fatty acid compounds were evaluated for their antimicrobial properties. The percentages of the composition for the tested compounds (crude PBC-FAs, crude SBC-FAs, crude soybean-phenolic BCFAs, crude linoleic-phenolic BCFAs, and crude linolenic-phenolic BCFAs) are listed in Tables 2 and 4. The compositions for the crude PBC-FAMEs (FIG. 3), and the crude TMS-PBC-FAMEs (FIG. 3) were not provided because they have the same compositions as the crude PBC-FAs as they were derived from the PBC-FA mixture. Since they were derived from the crude PBC-FAs, they should also have similar product mixture even though only one structure is shown in FIG. 1 for both compounds. The crude SBC-FA mixture had a different fatty acid composition (Table 2, Entry 5) because it was synthesized differently. This mixture was obtained from the reaction performed with OLA, H$^+$-Ferrierite, small amounts of triphenylphosphine and distilled water at 260° C. for 4 h. Since there was no phenol involved, this mixture should not contain any fatty acids with phenolic groups.

MICs and MBCs: Tables 5 and 6 list the MIC and MBC values of tested compounds against several Gram-positive and Gram-negative bacteria. The results indicated that MICs of the crude PBC-FA mixture against *Listeria innocua*, *Bacillus subtilis*, and *Enterococcus faecium* were surprisingly low at 1.8, 1.8, and 3.6 µg/mL, respectively. The MBCs of the crude PBC-FA mixture against *B. subtilis, E. faecium*, and *L. innocua* surprisingly were 1.8, 3.6, and 7.3 µg/mL, respectively, suggesting that the Gram-positive bacteria were surprisingly sensitive to the compounds and *B. subtilis* was the most sensitive among the three bacteria.

Although the crude PBC-FA mixture was surprisingly found to have excellent antimicrobial properties against Gram-positive bacteria, it was a mixture of various fatty acids. It was important to determine which fatty acids in the mixture were the active ingredients for the antimicrobial activity. Since the crude PBC-FAs contained predominantly phenolic branched-chain fatty acids (FIG. 1, structures 7 and 8), we speculated that it was these phenolic branched-chain fatty acids that played the essential roles against the bacteria. Since the phenolic fatty acids synthesized in the present study were not fatty acid esters but a fatty acid with phenolic group on various positions of the alkyl chain, it is likely these phenolic groups possess antimicrobial activity. In order to demonstrate this, control experiments were performed with various compounds including the crude SBC-FAs, crude PBC-FAMEs, and crude TMS-PBC-FAMEs.

The crude SBC-FA mixture (FIG. 1, structure 3) was chosen because the crude PBC-FAs contained about 30 wt % byproducts which should not play a role in the antimicrobial activities. To make sure this was the case, we decided to use the crude PBC-FA mixture as is because if the byproducts did not interfere with the studies, then no purification step is needed, saving cost and labor. As shown in Table 2, Entry 5, the SBC-FA mixture did not contain any phenolic branched-chain compounds (FIG. 1, structures 7 and 8), instead it contained compounds 3-6 in FIG. 1 (which was also in the crude PBC-FAs). There were also small amounts of dimer fatty acids in the mixture but these dimer acids did not have phenolic groups attached to the alkyl chain (Table 2, Entry 5). We hypothesized that if the SBC-FAs did not exhibit any antimicrobial activities, then the 30 wt % byproduct in the PBC-FA mixture did not play a role in the microbial activities. Control experiments with the crude SBC-FAs against Gram-positive bacteria were all above 232 µg/mL except that the MIC for SBC-FAs against *E. faecium* was 116 µg/mL (Table 5). These results showed that these byproducts did not play a role in the antimicrobial activities.

The crude PBC-FAMEs (FIG. 3, structure 1) and crude TMS-PBS-FAMEs (FIG. 3, structure 2) were used because the crude PBC-FAs had a hydrophilic carboxylic head and a hydrophobic long-chain fatty acid group attached with a phenolic group on various positions. We converted the hydrophilic carboxylic group in the crude PBC-FAs to ester derivative PBC-FAMEs to find out if the ester group would still have strong antimicrobial properties. Similar to the crude SBC-FAs, the MICs of crude PBC-FAMEs against Gram-positive bacteria were all above 232 µg/mL. These results showed that the hydrophilic carboxylic group in the fatty acids moiety was also important for the antimicrobial property of the phenolic branched-chain fatty acids.

To confirm that the hydroxyl group (i.e., phenolic group) of the compounds might play an important role in the antimicrobial property, the crude TMS-PBC-FAME mixture was tested. This crude TMS-PBC-FAME mixture was where the hydroxyl group has been protected by the trimethylsilyl group (FIG. 3). The results showed that the crude TMS- PBC-FAMEs against Gram-positive bacteria were all above 232 μg/mL. The results demonstrated that it was reasonable to predict that the mode of antimicrobial action of the compounds was due to actions of the fatty acids and phenols, and the antimicrobial activities of the phenolic fatty acid should be more than any of the individual group alone. This further confirmed that the phenolic fatty acids, having two hydrophilic portions (phenol and carboxylic group) and a hydrophobic region (alkyl chain in the fatty acid moiety), were good antimicrobials.

Another control experiment was performed using a mixture of 1:1 molar OLA and phenol. This experiment demonstrated the importance of the phenolic group being covalently attached to the fatty acids. The results showed that the mixture had a MIC of >232 μg/mL against Gram-positive bacteria.

The MICs of the tested compounds for all Gram-negative bacteria including *Escherichia coli, Pseudomonas tolaasii*, and *Salmonella enterica serovar Typhimurium* were all above 232 μg/mL (Table 5). Further tests using higher concentrations were conducted against *S. typhimurium* ATCC 53648). Results indicated that the MICs for crude PBC-FAs and crude sbc-FAs against *S. typhimurium* (ATCC 53648) were 1164 μg/mL and >2327 μg/mL, respectively. The MBC for compound crude PBC-FAs against *S. typhimurium* (ATCC 53648) was >2327 μg/mL. The results indicated branched-chain fatty acids with or without the phenolic active sites were surprisingly less active against Gram-negative bacteria.

Overall, compound crude PBC-FAs surprisingly had much higher antimicrobial ability than crude PBC-FAMEs, crude TMS-PBC-FAMEs, and SBC-FAs against Gram-positive bacteria. Our results surprisingly suggested that both the carboxylic group in the fatty acid moiety and the hydroxyl group in the phenol moiety were important for the antimicrobial properties of phenolic branched-chain fatty acids.

Figure 9:
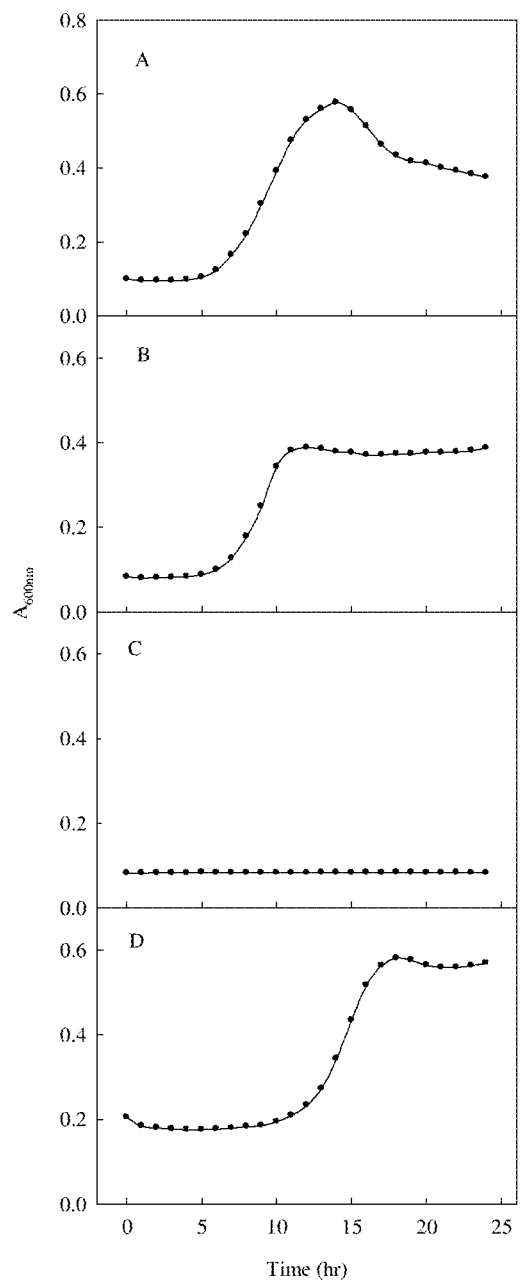
FIG. 9 shows growth curves of *Listeria innocua* during incubation at 37° C. as affected by crude PBC-FAs as described below.

Growth curves: The growth curves of the *L. innocua* in the presence and absence of crude PBC-FAs and SBC-FAs are shown in FIG. 9. The control samples showed typical growth curves with lag, exponential, stationary, and declining phases (FIG. 9A). The bacteria started the exponential phase at 5 h and reached a maximum population at 14 h and then decreased afterward. Samples treated with low concentration (0.9 μg/mL or lower) of crude PBC-FAs (FIG. 9B) showed a similar lag phase. However, the maximum bacterial population was surprisingly lower than the control sample. In addition, the population remained unchanged (without signs of declining) after reaching the maximum. The compound at concentration of 1.8 μg/mL surprisingly inhibited the growth of *L. innocua* (data not shown). Surprisingly crude PBC-FAs at higher concentration (i.e., 3.6 μg/mL or above) completely prevented the growth of *L. innocua* (FIG. 9C). Crude SBC-FAs, even at the highest concentration (232 μg/mL), did not prevent the bacterium reaching its maximum population (FIG. 9 D); however, the lag phase was longer compared to the control, i.e., the time reaching maximum was delayed by ~5 h by the compound.

Figure 10:
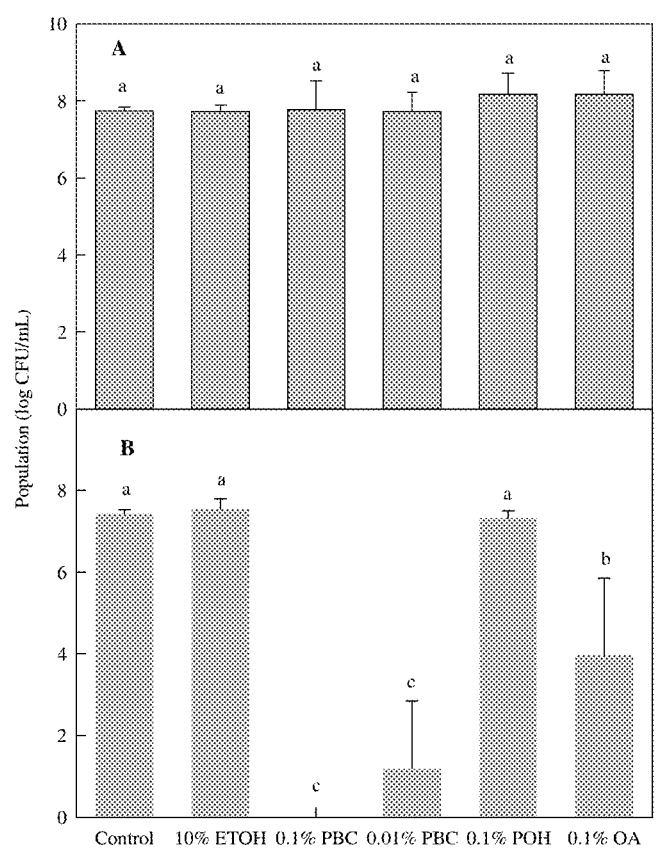
FIG. 10 shows the effect of crude PBC, phenol (POH) and OLA on populations of *E. coli* (FIG. 10A) and *Listeria innocua* (FIG. 10B) as described below. The bacteria were treated with control (not-treated), ethanol (ETOH), 0.1% and 0.01% phenol fatty acid (crude PBC-FAs), and 0.1% OLA for 5 min. Vertical bars represent standard deviations (n=3). Bars with same letters are not significantly different ($P<0.05$, Duncan's multiple range test).

Antimicrobial tests: Results showed that none of the compounds at the tested concentration had a significant effect on populations of Gram negative *E. coli* after 5 min treatment (FIG. 10A). For *L. innocua*, 10% ethanol and 0.1% phenol had no significant effect on the bacterial population compared to the control (FIG. 10B). The control sample had a bacterial population of 7.4 log CFU/ml. OLA at 0.1% significantly reduced the population of *L. innocua*; however the reduction was only 3.5 logs CFU/mL. The crude PBC-FA mixture at both 0.01 and 0.1% surprisingly reduced the population. The bacteria surprisingly became non-detectable (<1 CFU/mL) after 5 min treatment with 0.1% crude PBC-FA mixture, achieving more than 7 log reduction.

To improve the economics and antimicrobial activities, phenolic branched-chain fatty acid compounds derived from mixed fatty acids derived from various oils and phenolics were examined (Table 4). The antimicrobial activities of phenolic branched chain fatty acids synthesized from linoleic, linolenic acid, soybean fatty acids, and safflower fatty acids against *L. innocua* are shown in Table 7. The results surprisingly showed these compounds had lower MICs and MBCs and therefore better efficacy against *L. innocua* than the free fatty acids and phenolic themselves (Table 7).

Acne is one of the most common skin diseases, affecting more than 45 million individuals in the United States. *Propionibacterium acnes* is a gram-positive bacterium and human skin commensal that prefers anaerobic growth conditions and is involved in the pathogenesis of acne. It is also reported that *P. acnes* is associated with chronic prostatitis leading to prostate cancer, chronic recurrent multifocal osteomyelitis and synovitis-pustulosis-hyperostosis and osteitis syndrome, sarcoidosis, sciatica and various types of implant-associated infections. Our results showed that phenolic branched chain fatty acids were surprisingly effective against *P. acnes*, with a MIC and MBC of 3.6 and 7.2 μg/ml, respectively (Table 8). Phenol or mixture of OLA and phenol had MIC and MBC of more than 454 μg/ml, indicating the parent compounds surprisingly had little effect on the population of *P. acnes*. Our results indicated that the novel phenolic branched chain fatty acids may surprisingly be used to treated skin diseases and other infection caused by *P. acnes* (Table 8).

Our results demonstrated that the phenol fatty acids surprisingly had antimicrobial properties against Gram-positive bacteria. The mode of action is unclear.

In summary, our results suggest that the crude phenolic branched-chain fatty acid mixture had surprisingly strong antimicrobial properties against Gram-positive bacteria such as *L. innocua, B. subtilis*, and *E. faecium*. The antimicrobial ability was much stronger than equal molar mixture of phenol and OLA. The phenolic branched-chain fatty acids mixture was less effective against Gram-negative bacteria. By comparing with other synthesized phenolic branch-chained fatty acid analogs (esterification of fatty acid carboxyl group and trimethylsilylation of phenolic hydroxyl group), we demonstrated that the hydroxyl groups in the phenol and carboxyl group in the fatty acid group were surprisingly important in the antimicrobial ability against Gram-positive bacteria. Overall, our results surprisingly indicated the novel phenolic branch-chained fatty acids could be used to improve microbial safety of food.

All of the references cited herein, including U.S. Patents, are incorporated by reference in their entirety. Also incorporated by reference in their entirety are the following references: Christie, W. W., Lipid analysis: isolation, separation, identification, and structural analysis of lipids, 1982, Pergamon, New York; Lewis, P. T., et al., Tetrahedron, 56: 7805-7810 (2000); Delaquis, P. J., et al., Intern. J. Food Microbiol., 74: 101-109 (2002); Desbois AP, and V. J. Smith, Appl Microbiol Biotechnol., 85: 1629-1642 (2010); Kabara, J. J., et al., Antimicrob. Agents Chemother., 2: 23-28 (1972); Khalil, H., et al., Antimicrob. Agents Chemother., 52: 1635-1641 (2008); Kubo, I., et al., Bioorg. Med. Chem. Lett., 3: 1305-8. (1993a); Kubo et al. (Kubo, I., et al., Bioorganic & Medicinal Chemistry, 3: 873-880 (1995); Nakatani, N., Dev. Food Sci., 34: 251-271 (1994); Nazzaro, F., et al., Pharmaceuticals, 6(12): 1451-1474 (2013); Ultee, A., et al., App. Environ. Microbio., 68: 1561-1568 (2002); Niederl, J. B., and C. Liotta, J. Am. Chem. Soc., 55 (7): 3025-3026 (1933); Ouattara, B., et al., Intern. J. Food Microbiol., 37:155-162 (1997); Roe, E. T., et al., J. Am. Oil Chem. Soc., 36: 656-659 (1959); Rozès, N., and C. Peres, Appl. Microbiol. Biotechnol., 49:108-111 (1988); Torres de Pinedo, A. P., Food Chem., 105: 657-665 (2007); Occolowitz, J. L., Anal. Chem., 36: 2177-2181 (1964); Wang, J., and F. Shahidi, J. Agric. Food Chem., 62: 454-461 (2014); Kim, Y., et al., Intern. J. Antimic. Agents, 29: 217-222 (2007); U.S. patent application Ser. No. 12/767,083 filed on Apr. 26, 2010; U.S. patent application Ser. No. 12/774,347 filed on May 5, 2010; U.S. Provisional Application No. 61/640,276, filed 30 Apr. 2012.

Thus, in view of the above, the present invention concerns (in part) the following:

A method for preparing phenolic branched chain fatty acids or alkyl esters thereof, said process comprising (or consisting essentially of or consisting of) subjecting in a pressurized container (a) at least one phenolic compound, (b) unsaturated fatty acids having 6 to 25 carbon atoms, alkyl esters thereof, or mixtures thereof (e.g., soybean fatty acids or safflower fatty acids instead of oleic acid), and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain. The above method, wherein the ratio of said at least one phenolic compound: said unsaturated fatty acids or alkyl esters thereof is about 100 to about 1. The above method, wherein said unsaturated fatty acids have 10 to 22 carbon atoms. The above method, wherein said unsaturated fatty acids have 16 to 22 carbon atoms. The above method, wherein the number of unsaturated bonds in said unsaturated fatty acids is 1 to 3. The above method, wherein the yield of dimers is less than about 15 wt %. The above method, wherein the yield of linear chain fatty acid is less than about 18 wt %. The above method, wherein the conversion of said unsaturated fatty acids or alkyl esters thereof is greater than about 85%. The above process, wherein said process further comprises recycling said catalyst. The above process, wherein said process further comprises washing said catalyst with an acid solution or solvent and heating said catalyst. The above process, wherein said solvent is a polar solvent or non-polar solvent. The above process, wherein said catalyst is heated in an acid solution at about 55° C. for about 24 hours. The above process, wherein said catalyst is dried at about 115° C. for about 20 hours. The above process, wherein said catalyst is calcined at about 500° C. for at least 5 hours. The above process, said process comprising (or consisting essentially of or consisting of) subjecting in a pressurized container (a) at least two phenolic compounds, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenol on the fatty acid alkyl chain.

The above process, wherein said process does utilize any of the following catalysts: methanesulfonic acid; a solid superacid resin catalyst (e.g., a solid perfluorinated resin with perfluoro side chains containing sulfonic acid groups); clay catalysts (e.g., Montmorillonite K10, Montmorillonite KSF, bentonite, Kaolin, Panther Creek clay, talc, Clarion 470 and Clarion 550 clays (sold by American Colloid Company) and Montmorillonite K10 clay); highly acidic perfluorinated resins grafted with sulfonic acid; zeolite (i.e., Cu-Beta and H-Beta) and anion modified zirconia catalysts; anion modified sulfated and tungstated zirconia catalysts. The above process, wherein said process does not utilize any of the following catalysts: methanesulfonic acid; a solid superacid resin catalyst (e.g., a solid perfluorinated resin with perfluoro side chains containing sulfonic acid groups); clay catalysts (e.g., Montmorillonite K10, Montmorillonite KSF, bentonite, Kaolin, Panther Creek clay, talc, Clarion 470 and Clarion 550 clays (sold by American Colloid Company) and Montmorillonite K10 clay); highly acidic perfluorinated resins grafted with sulfonic acid; zeolite (i.e., Cu-Beta and H-Beta) and anion modified zirconia catalysts; anion modified sulfated and tungstated zirconia catalysts.

A method for killing microorganisms on or in an object, said method comprising (or consisting essentially of or consisting of) contacting said object with an effective microorganisms killing amount of a composition comprising (or consisting essentially of or consisting of) phenolic branched chain fatty acids or alkyl esters thereof, and optionally a carrier. The above method, wherein said phenolic branched chain fatty acids or alkyl esters thereof is produced by a method comprising (or consisting essentially of or consisting of) subjecting in a pressurized container (a) at least one phenolic compound, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain. The above method, where said microorganisms are selected for the group consisting of Gram-positive bacteria, Gram-negative bacteria, and mixtures thereof. The above method, where said microorganisms are Gram-positive bacteria. The above method, where said microorganisms are Gram-negative bacteria.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

H$^+$-Ferrierite-K zeolite catalyzed phenol additions to oleic acid (i.e., crude oleicphenol BCFA products).[a]

| | | | | GC weight percent | | | | | |
|---|---|---|---|---|---|---|---|---|---|
| Entry | Phenol [equiv. to OLA] | H-Ferr [wt % to OLA] | Temp [° C.] Time [hr] | $C_{18}$-Methyl-branched-chain FAs [SBC-FAs] [3][c] | $C_{18}$-Linear-chain FA [4][c] | Lactones [5&6][c] | Phenolic-branched-chain FAs [PBC-FAs] [7][c] | Dimer Phenolic FAs [8][c] | % conv.[b] |
| 1 | 1.2 | 10 | 200; 24 | 29.5 | 14.8 | 25.9 | 26.5 | 3.4 | 87.6 |
| 2 | 2 | 10 | 200; 24 | 18.8 | 15.9 | 26.9 | 35.2 | 3.24 | 86.4 |
| 3 | 4 | 10 | 200; 24 | 18.8 | 3.6 | 9.5 | 63.3 | 4.8 | 99 |
| 4 | 6 | 10 | 200; 6 | 13.7 | 14.8 | 35.8 | 33.3 | 2.4 | 87.6 |
| 5 | 6 | 10 | 200; 24 | 13.6 | 4.0 | 9.5 | 67.0 | 5.8 | 98.7 |
| 6 | 6 | 10 | 200; 48 | 12.3 | 3.2 | 7.2 | 72.3 | 5.0 | 99.5 |
| 7 | 6 | 15 | 200; 6 | 15.6 | 8.9 | 30.5 | 42.5 | 2.6 | 93.6 |
| 8 | 6 | 15 | 200; 24 | 9.7 | 1.8 | 6.5 | 73.9 | 8.1 | >99 |
| 9 | 6 | 15 | 200; 48 | 7.6 | 1.4 | 5.7 | 73.4 | 11.9 | >99 |
| 10 | 8 | 15 | 200; 6 | 13.2 | 10.0 | 28.4 | 43 | 5.4 | 92.5 |
| 11 | 8 | 15 | 200; 24 | 9.6 | 3.2 | 6.6 | 70.6 | 10.0 | 99.5 |
| 12 | 8 | 15 | 200; 48 | 10.3 | 2.7 | 8.5 | 73.0 | 5.5 | >99 |
| 13 | 6 | 20 | 200; 6 | 13.2 | 5.52 | 18.4 | 56 | 6.89 | 97.1 |
| 14 | 6 | 20 | 200; 24 | 9.09 | 1.83 | 6.03 | 75.1 | 7.95 | >99 |
| 15 | 6 | 20 | 200; 48 | 7.76 | 1.41 | 5.66 | 76 | 9.17 | >99 |
| 16 | 6 | 20 | 250; 6 | 22.5 | 2.8 | 5.9 | 59.6 | 9.2 | >99 |
| 17 | 6 | 20 | 250; 24 | 12.6 | 1.85 | 5.25 | 59.6 | 20.7 | >99 |
| 18 | 6 | 20 | 250; 48 | 9.58 | 1.63 | 4.59 | 64.5 | 19.7 | >99 |
| 19[d] | 6 | 15 | 200; 6 | 20.6 | 14.8 | 20.1 | 42.3 | 2.23 | 86 |
| 20[d] | 6 | 15 | 200; 24 | 15.2 | 2.22 | 5.81 | 69 | 7.78 | >99 |
| 21[d] | 6 | 15 | 200; 48 | 10.3 | 0.88 | 5.55 | 73.7 | 8.56 | >99 |

[a]Products were isomerized/arylated, hydrogenated, methylated, and analyzed by GC. Results were compared against internal standard (C13:0). OLA (91.2 wt % C18:1, 6.1 wt % C18:2, 2.7 wt % C18:0; UFA = 97.3%). H-Ferr. = H-Ferrierite; UFA = unsaturated fatty acid; OLA = oleic acid; 97.3 = UFA in OLA; 2.7 = C18:0 in OLA.
[b]% Conversion = (97.3 − (C18-linear-chain FA-2.7))/97.3 × 100
[c]Refering to FIG. 1
[d]Methyl oleate (99% pure)

TABLE 2

H$^+$-Ferrierite-K zeolite catalyzed reactions using oleic acid.[a]

| | GC weight percent composition | | | | | | |
|---|---|---|---|---|---|---|---|
| Entry | $C_{18}$-Methyl-branched-chain FAs [SBC-FAs] [3][c,d] | $C_{18}$-Linear-chain FA [4][c,d] | Lactones [5&6][c,d] | Phenolic-branched-chain FAs [PBC-FAs] [7][c,d] | Dimer Phenolic FAs [8][c,d] | Dimer fatty acids | % Conv. |
| 1[b,c] | 9.24 | 3.25 | 10.3 | 70.6 | 6.61 | 0 | 93.9 |
| 2[b,c] | 8.61 | 4.84 | 7.50 | 70.5 | 8.55 | 0 | 92.3 |
| 3[b,c] | 10.1 | 3.10 | 9.42 | 70.0 | 7.38 | 0 | 94.0 |
| 4[b,c] | 9.80 | 3.20 | 9.50 | 72.3 | 5.20 | 0 | 93.9 |
| 5[d,e] | 73.6 | 6.80 | 11.1 | 0 | 0 | 8.50 | 98.9 |

[a]To characterize these products using GC, the products had to be hydrogenated and methylated. Methyl tridecanoate ($C_{13:0}$) was used as internal standard. [b]The reactions were carried OLA (180 g), 8.0 equivalent of phenol (487 g), H$^+$-Ferrierite-K zeolite (27 g, 15 wt % to OLA), and distilled water (19.4 mL, 10.8% to OLA) at 200° C. for 24 h. [c]Conversion = [(97.3 − (stearic acid) − 2.7)]/97.3 × 100. {97.3 is the total unsaturated fatty acids in the OLA which contribute to the reaction. 2.7 is the stearic acid in the OLA which does not contribute to the reaction.} [d]The reaction was carried OLA (50 g), H$^+$-Ferrierite zeolite (2.5 g, 5.0 wt % to OLA), of triphenylphosphine (13 mg, 0.5 wt % to zeolite), and distilled water (1.8 mL, 3.6% to OLA) at 260° C. for 4 h. [e]Conversion = 94.3 − [(stearic acid − 5.74)]/94.3 ×100. {94.3 is the total unsaturated fatty acids in the OLA which contribute to the reaction. 5.74 is the fatty acids in the OLA which do not contribute to the reaction.}
[d]Refering to FIG. 1

TABLE 3

H+-Ferrierite-K zeolite catalyzed phenol additions to soybean fatty acids.[a]

| Entry | Phenol [equiv. to soybean FAs] | H-Ferr [wt % to Soybean FAs] | Water [% to H-Ferr] | Temp [°C.] Time [hr] | Methyl-branched-chain [SBC-FAs] FAs [3][d] | Lactones [5&6][d] | Phenolic-branched-chain FAs [PBC-FAs, 7][d] [poly-PBC-FAs, 1&2][e] | Dimer phenolic branched-chain FAs [8][d] | % Conv.[c] |
|---|---|---|---|---|---|---|---|---|---|
| 1 | 6 | 5 | 73 | 200; 6 | 0.0 | 5.1 | 37 | 6.0 | 48 |
| 2 | 6 | 5 | 73 | 200; 24 | 4.2 | 7.8 | 56 | 17 | 85 |
| 3 | 6 | 5 | 73 | 200; 48 | 6.1 | 9.7 | 62 | 15 | 92 |
| 4 | 6 | 10 | 73 | 200; 6 | 5.3 | 11 | 57 | 3.4 | 77 |
| 5 | 6 | 10 | 73 | 200; 24 | 10 | 17 | 54 | 11 | 93 |
| 6 | 6 | 10 | 73 | 200; 48 | 8.6 | 11 | 68 | 19 | 100 |
| 7 | 6 | 15 | 73 | 200; 6 | 7.7 | 14 | 65 | 12 | 99 |
| 8 | 6 | 15 | 73 | 200; 24 | 8.7 | 11 | 65 | 22 | 100 |
| 9 | 6 | 15 | 73 | 200; 48 | 6.6 | 4.6 | 71 | 27 | 100 |
| 10[f] | 6 | 15 | 0 | 200; 6 | 6.8 | 7.3 | 49 | 3.4 | 66 |
| 11[f] | 6 | 15 | 0 | 200; 24 | 12 | 11 | 65 | 5.8 | 93 |
| 12[f] | 6 | 15 | 0 | 200; 48 | 18 | 12 | 64 | 7.0 | 100 |

[a]Products were isomerized/arylated, hydrogenated, methylated, and analyzed by GC. Results were compared against internal standard (C13:0). Soybean FAs (14.8 wt % C16:0, 7.03 wt % C18:0, 22.8 wt % C18:1, 43.2 wt % C18:2, 5.96 wt % C18:3, 6.21 wt % unknown; 78.2% of the starting unsaturated fatty acids contribute to the reaction)
[b]Percent yield = [GC wt % of component]/78.2
[c]% conversion of soybean FAs = sum of GC wt % (methyl-branched-chain FAs + lactones + phenolic branched fatty acids + dimer)/78.2 × 100
[d]Refering to FIG. 1
[e]Refering to FIG. 2
[f]Reactions were performed without water.

TABLE 4

H+- Ferrierite-NH4-500 zeolite catalyzed phenolic additions to unsaturated polymeric fatty acids.[a]

| Entry | Feedstock | Phenolic | Phenol [equiv. to feedstock] | H-Ferr [wt % to feedstock] | Water [% to H-Ferr] | Temp [°C.] Time [hr] | Methyl-branched-chain FAs [SBC-FAs] [3][p] | Lactones [5&6][p] | Phenolic-branched-chain FAs [PBC-FAs, 7][p] [poly-PBC-FAs, 1&2][q] | Dimer phenolic FAs [8][p] | % Conv. | Product Name |
|---|---|---|---|---|---|---|---|---|---|---|---|---|
| 1 | Soybean FAs[b,c,d] | phenol | 6 | 10 | 430 | 260, 24 | 10 | 6.2 | 73 | 19 | 100 | Crude soybean-phenolic BCFAs |
| 2 | Soybean FAs[b,c,d,e] | Phenol | 6 | 10 | 430 | 260, 24 | 13 | 9.8 | 71 | 17 | 100 | Crude soybean-phenolic BCFAs |
| 3 | Soybean FAs[b,c,d,f] | Phenol | 6 | 10 | 650 | 260, 24 | 13 | 2.1 | 73 | 17 | 100 | Crude soybean-phenolic BCFAs |
| 4 | Safflower FAs[g,h,i] | Phenol | 6 | 5 | 650 | 260 8 | 9.6 | 5.5 | 75.8 | 12.9 | 100 | Crude safflower-phenol BCFAs |
| 5 | Safflower FAs[g,h,i] | Thymol | 6 | 10 | 650 | 260, 24 | 8.8 | 10.6 | 62.6 | 2.9 | 85 | Crude safflower-thymol BCFAs |
| 6 | Safflower FAs[g,h,i] | creosote | 6 | 10 | 650 | 260, 24 | 10.7 | 5.6 | 77 | 2.3 | 96 | Crude safflower-creosote BCFAs |
| 7 | Safflower FAs[g,h,i] | carvacrol | 6.5 | 10 | 650 | 260, 48 | 18.8 | 15.2 | 44.7 | 4.4 | 83 | Crude safflower-carvacrol BCFAs |
| 8 | Linoleic Acid[j,k,l] | Phenol | 6 | 10 | 650 | 260, 24 | 0 | 1.6 | 73.2 | 25 | 100 | Crude linoleic-phenolic BCFAs |

TABLE 4-continued

H+- Ferrierite-NH4-500 zeolite catalyzed phenolic additions to unsaturated polymeric fatty acids.[a]

| Entry | Feedstock | Phenolic | Phenol [equiv. to feedstock] | H-Ferr [wt % to feedstock] | Water [% to H-Ferr] | Temp [°C.] Time [hr] | Methyl-branched-chain FAs [SBC-FAs] [3][p] | Lactones [5&6][p] | Phenolic-branched-chain FAs [PBC-FAs, 7][p] | Dimer phenolic FAs [poly-PBC-FAs, 1&2][q] | % Conv. | Product Name |
|---|---|---|---|---|---|---|---|---|---|---|---|---|
| 9 | Linolenic acid[m,n,o] | phenol | 6 | 10 | 650 | 260, 24 | 2.9 | 5.6 | 41.7 | 54.7 | 100 | Crude linolenic-phenolic BCFAs |

[a]Products were isomerized/arylated, hydrogenated, methylated, and analyzed by GC. Results were compared against internal standard (C13:0).
[b]Soybean FAs (14.8 wt % C16:0, 7.03 wt % C18:0, 22.8 wt % C18:1, 43.2 wt % C18:2, 5.96 wt % C18:3, 6.21 wt % unknown; 78.2% of the starting unsaturated fatty acids contribute to the reaction)
[c]Percent yield = [GC wt % of component]/78.2
[d]% conversion of soybean FAs = sum of GC wt % (methyl-branched-chain FAs + lactones + phenolic branched fatty acids + dimer)/78.2 × 100
[e]Repeat of Entry 1 but scaled up to 10 times
[f]Repeat of Entry 2 but increased the water content
[g]Safflower FAs (9.57 wt % C16:0; 3.77 wt % C18:0, 21.5 wt % C18:1, 65.2 wt % C18:2; 86.7% of the starting unsaturated fatty acids contribute to the reaction)
[h]Percent yield = [GC wt % of component]/86.7
[i]% conversion of safflower FAs = sum of GC wt % (methyl-branched-chain FAs + lactones + phenolic branched fatty acids + dimer)/86.7 × 100
[j]Linoleic acid (99 wt % C18:2)
[k]% yield = [GC wt % of component]/99.9
[l]% conversion of linoleic = sum of GC wt % (methyl-branched-chain FAs + lactones + phenolic branched fatty acids + dimer)/99.9 × 100
[m]Linolenic acid (9.63 wt % C16:0, 6.77 wt % C18:0, 30.3 wt % C18:1, 16.5 wt % C18:2, 1.41 wt % C20:0, 35.4 wt % C18:3, 82.2% of the starting unsaturated fatty acids contribute to the reaction)
[n]% yield = [GC wt % of component]/82.2
[o]% conversion of linolenic = sum of GC wt % (methyl-branched-chain FAs + lactones + phenolic branched fatty acids + dimer)/82.2 × 100
[p]Referring to FIG. 1
[q]Referring to FIG. 2

TABLE 5

MICs of PBC-FAs against Gram-positive and negative bacteria.[a]

| Microorganism | Gram type | Crude phenolic branched-chain fatty acid mixture (PBC-FAs)[a] | Crude phenolic branched-chain fatty acid methyl ester mixture (PBC-FAMEs)[a] | Crude unsaturated methyl branched fatty acid mixture (SBC-FAs)[b] | Oleic acid & phenol |
|---|---|---|---|---|---|
| | | MIC (μg/ml) | | | |
| *Bacillus subtilis* ATCC 6633 | + | 1.8 | >232 | >232 | >232 |
| *Enterococcus faecium* ATCC 8459 | + | 1.8 | >232 | 116 | >232 |
| *Listeria innocua* ATCC 33090 | + | 3.6 | >232 | >232 | >232 |
| *Pseudomonas tolaasii* #67 Isolate e.b. | − | >232 | >232 | >232 | >232 |
| *Escherichia coli* K12 ATCC 23716 | − | >232 | >232 | >232 | >232 |
| *Escherichia coli* ATCC 25922 | − | >232 | >232 | >232 | >232 |
| *Escherichia coli* O157:H7 ATCC 700728 | − | >232 | >232 | >232 | >232 |
| *Salmonella enterica* serovar Typhimurium ATCC 53647 | − | >232 | >232 | >232 | >232 |
| *Salmonella enterica* serovar Typhimurium ATCC 53648 | − | >232 | >232 | >232 | >232 |

[a]See Table 2, Entries 1-4 for PBC-FAs compositions.
[a]See Table 2, Entry 5 for SBC-FAs compositions.

TABLE 6.

MBCs of PBC-FAs against Gram-positive and negative bacteria.[a]

| Microorganism | Gram type | Crude phenolic branched-chain fatty acid mixture (PBC-FAs)[a] | MBC (μg/ml) Crude phenolic branched-chain fatty acid methyl ester mixture (PBC-FAMEs)[a] | Crude unsaturated methyl branched fatty acid mixture (SBC-FAs)[c] | Oleic acid & phenol |
|---|---|---|---|---|---|
| Bacillus subtilis ATCC 6633 | + | 1.8 | —[b] | —[b] | —[b] |
| Enterococcus faecium ATCC 8459 | + | 3.6 | —[b] | 116 | —[b] |
| Listeria innocua ATCC 33090 | + | 7.3 | >232 | >232 | >232 |
| Pseudomonas tolaasii #67 Isolate e.b. | − | >232 | >232 | <232 | <232 |
| Salmonella enterica Typhimurium ATCC 53647 | − | >232 | >232 | —[b] | —[b] |
| Salmonella enterica Typhimurium ATCC 53648 | − | >2327 | —[b] | —[b] | —[b] |

[a]See Table 2, Entries 1-4 for PBC-FAs compositions.
[b]MBC test was not carried on because the MICs in Table 5 were high.
[c]See Table 2, Entry 5 for SBC-FAs compositions.

TABLE 7

MIC and MBC of phenolic branched chain fatty acids against L. innocua ATCC 33090[a]

| Compound | MIC (μg/ml) | MBC (μg/ml) |
|---|---|---|
| Crude soybean-phenol BCFAs[b] | 3.6 | 7.2 |
| Crude linoleic-phenol BCFAs[c] | 3.6 | 7.2 |
| Crude linolenic-phenol BCFAs[d] | 7.2 | 14.6 |
| Crude safflower-phenol BCFAs[e] | 7.2 | 14.6 |
| Crude safflower-thymol BCFAs[f] | 14.6 | >232.7 |
| Crude safflower-creosote BCFAs[g] | 7.2 | 58.2 |
| Crude safflower-carvacrol BCFAs[h] | 116.4 | >232.7 |
| Phenol | >454.5 | >454.5 |
| Thymol | >232.7 < 454.5 | >454.5 |
| Creosote | >454.5 | >454.5 |
| Carvacrol | >232.7 < 454.5 | 454.5 |
| Soybean fatty acid[i] | >454.5 | >454.5 |
| Soybean fatty acid + phenol (1 mol:1.5 mol) | >454.5 | >454.5 |
| Safflower fatty acid[j] | >454.5 | >454.5 |
| Safflower fatty acid + phenol (1 mol:2.86 mol) | >454.5 | >454.5 |
| Safflower fatty acid + thymol (1 mol:1.47 mol) | >454.5 | >454.5 |
| Safflower fatty acid + carvacrol (1 mol:1.1 mol) | >454.5 | >454.5 |
| Safflower fatty acid + creosote (1 mol:0.84 mol) | >454.5 | >454.5 |

[a]MIC and MBC experiments were performed in three replicates.
[b]See Table 4, Entry 1 for Crude soybean-phenolic BCFAs compositions.
[c]See Table 4, Entry 8 for Crude linoleic-phenolic BCFAs compositions.
[d]See Table 4, Entry 9 for Crude linolenic-phenolic BCFAs compositions.
[e]See Table 4, Entry 4 for Crude safflower-phenolic BCFAs compositions
[f]See Table 4, Entry 5 for Crude safflower-thymol BCFAs compositions
[g]See Table 4, Entry 6 for Crude safflower-creosote BCFAs compositions
[h]See Table 4, Entry 7 for Crude safflower-carvacrol BCFAs compositions
[i]Soybean FAs (14.8 wt % C16:0, 7.03 wt % C18:0, 22.8 wt% C18:1, 43.2 wt % C18:2, 5.96 wt % C18:3, 6.21 wt% unknown; 78.2% of the starting unsaturated fatty acids contribute to the reaction)
[j]Safflower FAs (9.57 wt % C16:0; 3.77 wt % C18:0, 21.5 wt % C18:1, 65.2 wt % C18:2; 86.7% of the starting unsaturated fatty acids contribute to the reaction)

TABLE 8

MIC and MBC of phenolic branched chain fatty acids against Propionibacterium acnes.[a]

| Compound | MIC (μg/ml) | MBC (μg/ml) |
|---|---|---|
| PBC-FAs[b] | 3.6 | 7.2 |
| Crude soybean-phenolic BCFAs[c] | 3.6 | 7.2 |
| Crude linoleic-phenolic BCFAs[d] | 3.6 | 7.2 |
| Crude linolenic-phenolic BCFAs[e] | 14.6 | 29.1 |
| Phenol | >2327 | >2327 |
| Oleic acid + phenol (1 mol:1 mol) | >454.5 | >454.5 |
| Soybean fatty acid | >454.5 | >454.5 |
| Soybean fatty acid + phenol (1 mol:1.5 mol) | >454.5 | >454.5 | aEach MIC and MBC experiments were performed in three replicates.
[b]See Table 2, Entries 1-4 for PBC-FAs compositions
[c]See Table 4, Entry 1 for Crude soybean-phenolic BCFAs compositions.
[d]See Table 4, Entry 8 for Crude linoleic-phenolic BCFAs compositions.
[e]See Table 4, Entry 9 for Crude linolenic-phenolic BCFAs compositions

We claim:

1. A method for killing microorganisms on or in an object, said method comprising contacting said object with an effective microorganisms killing amount of a composition comprising phenolic branched chain fatty acids or alkyl esters thereof, and optionally a carrier.

2. The method according to claim 1, wherein said phenolic branched chain fatty acids or alkyl esters thereof is produced by a method comprising subjecting in a pressurized container (a) at least one phenolic compound, (b) unsaturated fatty acids having 6 to 25 carbon atoms, alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain.

3. The method according to claim 1, where said microorganisms are selected for the group consisting of Gram-positive bacteria, Gram-negative bacteria, and mixtures thereof.

4. The method according to claim 1, where said microorganisms are Gram-positive bacteria.

5. The method according to claim 1, where said microorganisms are Gram-negative bacteria.

6. The method according to claim 1, where said phenolic branched chain fatty acids or alkyl esters thereof is a mixture of phenolic branched chain fatty acids or alkyl esters thereof.

7. The method according to claim 6, wherein said mixture of phenolic branched chain fatty acids or alkyl esters thereof is produced by a method comprising subjecting in a pressurized container (a) at least one phenolic compound, (b) a mixture of unsaturated fatty acids having 6 to 25 carbon atoms, a mixture of alkyl esters thereof, or mixtures thereof, and (c) H-ferrierite zeolite catalyst in the presence of distilled water or alcohol and a nitrogen atmosphere at a temperature of about 100° C. to about 400° C. and a pressure of about 10 to about 1000 psi, and isolating saturated phenolic branched chain fatty acids or alkyl esters thereof or mixtures thereof; wherein the ratio of said at least one phenolic compound: said unsaturated fatty acids or alkyl esters thereof is about 100 to about 1, wherein the yield of said saturated phenolic branched chain fatty acids is greater than about 70 wt %, and wherein there is at least one phenolic on the fatty acid alkyl chain; where the number of unsaturated bonds in said unsaturated fatty acids is 3; wherein said process produces phenolic branched chain fatty acids or alkyl esters thereof having one phenol on the fatty acid alkyl chain, wherein said process produces phenolic branched chain fatty acids or alkyl esters thereof having two phenols on the fatty acid alkyl chain, and wherein said process produces phenolic branched chain fatty acids or alkyl esters thereof having three phenols on the fatty acid alkyl chain.

* * * * *